US008168028B2

(12) United States Patent
Schneider et al.

(10) Patent No.: US 8,168,028 B2
(45) Date of Patent: May 1, 2012

(54) METHOD AND APPARATUS FOR MAKING ARTICLE HAVING SIDE SEAMS

(75) Inventors: Uwe Schneider, Cincinnati, OH (US); Jeffrey Alan Darner, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 48 days.

(21) Appl. No.: 12/794,143

(22) Filed: Jun. 4, 2010

(65) Prior Publication Data
US 2010/0236703 A1 Sep. 23, 2010

Related U.S. Application Data

(62) Division of application No. 11/543,597, filed on Oct. 5, 2006, now Pat. No. 7,753,099.

(51) Int. Cl.
*B32B 37/00* (2006.01)
*B32B 37/02* (2006.01)
*B32B 38/00* (2006.01)
*B32B 38/04* (2006.01)

(52) U.S. Cl. ......... 156/264; 156/250; 156/256; 156/269
(58) Field of Classification Search .................. 156/250, 156/256, 264, 269
See application file for complete search history.

(56) References Cited

U.S. PATENT DOCUMENTS

| RE26,151 E | 1/1967 | Duncan et al. |
| 3,728,191 A | 4/1973 | Weirzba et al. |
| 3,860,003 A | 1/1975 | Buell |
| 4,482,666 A | 11/1984 | Reeves |
| 4,515,595 A | 5/1985 | Kievit et al. |
| 4,573,986 A | 3/1986 | Minetola et al. |
| 4,610,678 A | 9/1986 | Weisman et al. |
| 4,673,402 A | 6/1987 | Weisman et al. |
| 4,695,278 A | 9/1987 | Lawson |
| 4,799,611 A | 1/1989 | Taga |

(Continued)

FOREIGN PATENT DOCUMENTS

EP 0 717 971 A1 6/1996

(Continued)

OTHER PUBLICATIONS

International Search Report dated Jan. 25, 2008, 12 pages.

*Primary Examiner* — Mark A Osele
*Assistant Examiner* — Christopher C Caillouet
(74) *Attorney, Agent, or Firm* — Charles R. Matson

(57) ABSTRACT

A method for forming an undergarment comprises providing a web, cutting the web to form a pre-form, the pre-form comprising the first and the second transverse edges and two longitudinal edges, each longitudinal edge having two waist sections and a crotch section located intermediate the waist sections, a sealing area being located adjacent and inboard of each waist section, and transferring the pre-form to a processing wheel. The method further comprises gripping the pre-form adjacent each waist section with the grippers in four gripping areas, each gripping area being located near a respective sealing area, jointly rotating at least the grippers that hold the gripping areas in the region of one of the transverse edges around at least one hinging axis extending substantially parallel to the transverse edges of the pre-form to place the transverse edge generally parallel and opposite to the second transverse edge, superimposing the sealing areas in a contacting relationship, joining the superimposed sealing areas, thus forming the undergarment, and releasing the undergarment from the grippers.

12 Claims, 23 Drawing Sheets

U.S. PATENT DOCUMENTS

| | | | |
|---|---|---|---|
| 4,834,735 A | 5/1989 | Alemany et al. | |
| 4,842,666 A | 6/1989 | Werenicz | |
| 4,888,231 A | 12/1989 | Angstadt | |
| 4,909,803 A | 3/1990 | Aziz et al. | |
| 5,151,092 A | 9/1992 | Buell et al. | |
| 5,779,831 A | 7/1998 | Schmitz | |
| 7,322,925 B2 | 1/2008 | Couillard et al. | |
| 2003/0111168 A1 | 6/2003 | Olson et al. | |
| 2006/0135928 A1* | 6/2006 | Karlsson et al. | 604/385.11 |
| 2008/0083489 A1 | 4/2008 | Schneider | |

FOREIGN PATENT DOCUMENTS

| | | |
|---|---|---|
| EP | 0 717 972 A1 | 6/1996 |
| WO | WO 03/051248 | 6/2003 |
| WO | WO 2004/062541 | 7/2004 |
| WO | WO 2007/070113 | 6/2007 |

* cited by examiner

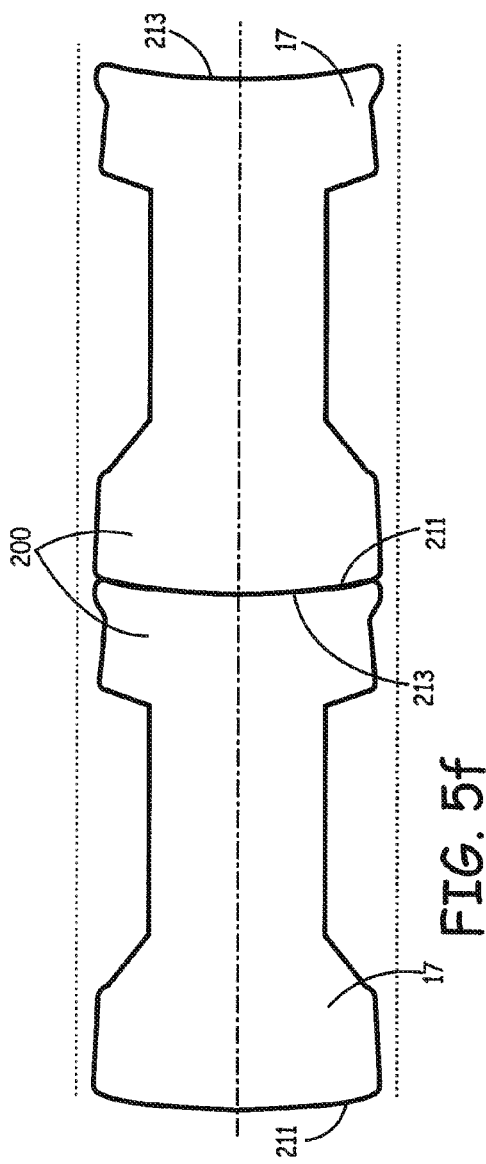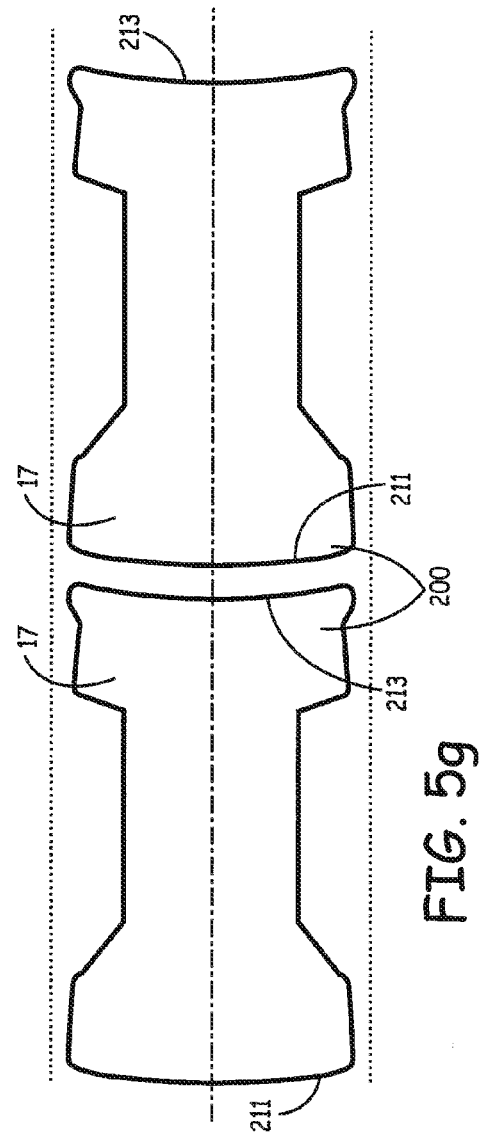

METHOD AND APPARATUS FOR MAKING ARTICLE HAVING SIDE SEAMS

CROSS REFERENCE TO RELATED APPLICATION

This application is a divisional of U.S. application Ser. No. 11/543,597, filed on Oct. 5, 2006, now U.S. Pat. No. 7,753,099 which is incorporated by reference herein.

FIELD OF THE INVENTION

The invention relates to a method of making an undergarment having side seams from a substantially two-dimensional web, the web having two longitudinal sides and a first transverse edge extending transversely to the longitudinal sides.

BACKGROUND OF THE INVENTION

Infants and other incontinent individuals wear absorbent articles such as diapers to absorb and retain urine and other body exudates. Absorbent articles function both to contain the discharged materials and to isolate these materials from the body of the wearer and from the wearer's garments and bed clothing. Disposable absorbent articles having many different basic designs are described, for example, in U.S. Pat. No. Re. 26,151 and U.S. Pat. No. 3,860,003.

Diapers that have achieved increasing commercial success in recent years are pull-on pant-type diapers or training pants. Diapers are used with infants prior to toilet training. The training pant is intended for use when the child has reached an age at which he or she is ready to graduate to an underpant type of garment as a replacement for disposable diapers previously used. Training pants have a "closed" chassis configuration, in which the chassis is adapted to be pulled on over the legs and lower torso of the wearer without any additional fastening steps.

Closed chassis diapers can be manufactured using a unibody design or a multi-piece design. In a multi-piece design, there are typically at least three chassis components that form the diaper: a crotch component, a front ear component, and a back ear component. Very generally, the crotch component extends in the long direction from the front to the back, and the front ear component and the back ear component extend in the long direction from one side to the other. The front ear component is attached to a front edge of the crotch component and the rear component is attached to a rear edge of the crotch component. A generally hour-glass configuration is thus achieved. A unibody design involves a single component that is shaped as desired. Thus, a rectangular piece may be shaped by notching the sides in the crotch area. Regardless of whether a multi-piece design or a unibody design is used, the front ear is seamed to the back ear to form the closed chassis.

Absorbent articles may have manually tearable side seams. The seams may be butt-type seams or overlapping side seams. An underpant may be manufactured from a blank cut to a suitable configuration. Layers of the diaper are built up on the blank cut and, after being fully assembled, the blank is folded along its central transverse area and the sides of the front and rear panels are seamed together to form the finished underpant. Alternatively, the seams may be formed by folding the chassis in the crotch portion so that the longitudinal side regions of the front portion and rear portion are superposed to form seaming areas, and then treating each seaming area with ultrasonic energy to sever the material in the seaming area in a first area while simultaneously bonding the material of the seaming area in a marginal area adjacent the first area to form a flangeless seam. This may form a splice between the front portion and the rear portion of the chassis.

It would be advantageous to provide a method for producing an article such as a training pant having side seams that produces the training pants at a high rate. It would further be advantageous to provide an apparatus for carrying out such method, which apparatus is of relatively simple construction, and allows high-speed formation of the side seams.

SUMMARY OF THE INVENTION

A method for making absorbent articles such as training pants and diapers is provided. An apparatus for carrying out such method is further provided.

A method of making an undergarment having side seams from a substantially two-dimensional web is provided. In one embodiment the method comprises cutting the web to form a two-dimensional pre-form, the pre-form comprising the first and the second transverse edge and two longitudinal edges, each longitudinal edge having two waist sections and a crotch section located intermediate the waist sections, a sealing area being located adjacent and inboard of each waist section, transferring the pre-form to a processing wheel wherein transferring comprises gripping the pre-form at each transverse edge using a vacuum transfer bar, and transferring the pre-form from the vacuum transfer bar to a gripper. The method further comprises gripping the pre-form adjacent each waist section with the gripper in four gripping areas, each gripping area being located near a respective sealing area, jointly rotating at least the gripper holding the gripping areas in the region of one of the transverse edges around at least one hinging axis extending substantially parallel to the transverse edges of the pre-form to place the transverse edge generally parallel and opposite to the second transverse edge, superimposing the sealing areas in a contacting relationship, joining the superimposed sealing areas, thus forming the undergarment, and releasing the undergarment from the gripper.

An apparatus for making an undergarment having side seams from a substantially two-dimensional web is provided, where the web has a processing wheel with at least one processing station. The web is cut to form a pre-form comprising first and second transverse edges and first and second longitudinal edges, each longitudinal edge having two waist sections and a crotch section located intermediate the waist sections, and a sealing area being located adjacent and inboard of each waist section.

In one embodiment, the apparatus has at least two processing stations and each processing station comprises a frame, carrier arms, each carrier arm being coupled to the frame and mounted on a hinging axis extending generally transversely to the carrier arms and substantially parallel to the transverse edges of the pre-form, and four grippers that grip the pre-form in gripping areas, each gripping area being located near a respective sealing area and each gripper being coupled to a carrier arm. A carrier arm actuator is provided for rotating the carrier arm around its hinging axis to a folded configuration, the carrier arm actuator comprising a lower member and a connecting arm, the connecting arm being hingeably connected to the lower member. A vacuum transfer bar is provided between adjacent processing stations.

According to another embodiment, each processing station comprises a frame, carrier arms, each carrier arm being coupled to the frame and mounted on a hinging axis extending generally transversely to the carrier arms and substantially parallel to the transverse edges of the pre-form, and four grippers that grip the pre-form in gripping areas, each gripping area being located near a respective sealing area, each gripper being coupled to a carrier arm. A carrier arm actuator is provided for rotating the carrier arm around its hinging axis to a folded configuration, the carrier arm actuator comprising a lower member and a connecting arm, the connecting arm being hingeably connected to the lower member. At least one retractable linear guiding mechanism is provided for controlling the motion of the gripper and having the ability to contract in length.

According to yet a further embodiment, each processing station comprises a frame, carrier arms, each carrier arm being coupled to the frame and mounted on a hinging axis extending generally transversely to the carrier arms and substantially parallel to the transverse edges of the pre-form, and four grippers that grip the pre-form in gripping areas, each gripping area being located near a respective sealing area, each gripper being coupled to a carrier arm. A carrier arm actuator is provided for rotating the carrier arm around its hinging axis to a folded configuration, the carrier arm actuator comprising a lower member and a connecting arm, the connecting arm being hingeably connected to the lower member. A motion stop is provided for limiting vertical movement of the grippers.

While multiple embodiments are disclosed, still other embodiments of the invention will become apparent to those skilled in the art from the following detailed description, which shows and describes illustrative embodiments of the invention. As will be realized, the invention is capable of modifications in various obvious aspects, all without departing from the spirit and scope of the invention. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the present invention, it is believed that the invention will be better understood from the following description, which is taken in conjunction with the accompanying drawings in which like designations are used to designate substantially identical elements, and in which:

FIG. 5f shows a continuous web after side notching and a curved final knife cut is performed in accordance with one embodiment wherein no trim is provided between individual blanks.

FIG. 5g shows a continuous web after side notching and a curved final knife cut is performed in accordance with one embodiment wherein trim is provided between individual blanks.

DETAILED DESCRIPTION OF THE INVENTION

Figure 1:
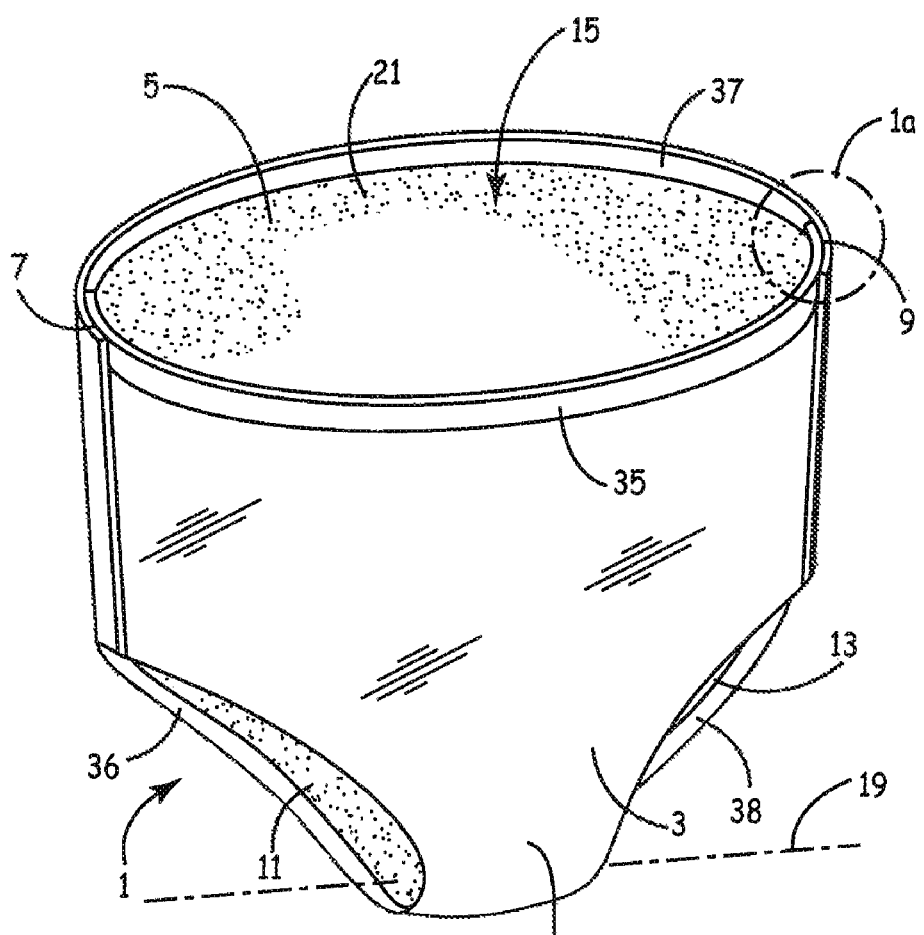
FIG. 1 shows an article having overlapping seams.

A method for making absorbent articles such as training pants and diapers is provided. For the purposes of illustration, the articles may be referred to herein as training pants, undergarments, garments, or diapers, and no limitations are intended by such reference.

As used herein, the term "absorbent article" refers to devices that absorb and contain body exudates. Absorbent articles may be placed against or in proximity to the body of the wearer to absorb and contain the various exudates discharged from the body. Absorbent articles include devices designed to absorb urine, which are used by incontinent persons. Such incontinent articles include but are not limited to diapers, adult incontinent briefs, training pants, diaper holders, and liners. Other absorbent articles include those designed to absorb blood-based fluids such as menses. Such sanitary hygiene articles include tampons, catamenial pads, and the like. The term "disposable" is used herein to describe absorbent articles that are not intended to be laundered or otherwise restored or reused as an absorbent article (i.e., they are intended to be discarded after a single use and, optionally, to be recycled, composted or otherwise disposed of in an environmentally compatible manner).

As used herein, the term "absorbent core" refers to the portions (e.g., layers) of an absorbent article that function to acquire, distribute, transfer, store, and/or redistribute fluid. Acquisition materials include materials whose primary function is to acquire, and then relinquish, fluids. Such materials include acquisition layers, topsheet materials, transfer layers, flow control modules, wrap tissues, or nonwoven sheets designed to prevent migration of hydrogel forming polymers, etc. As used herein, the term "distribution material" refers to the absorbent core material(s) whose primary function is to absorb and distribute/redistribute fluid to points away from the point of initial fluid loading. As used herein, the term "storage material" refers to the absorbent core material that retains a majority of the fluid retained, on a weight basis. It should be understood that the terms "distribution material" and "storage material" are not mutually exclusive. In certain embodiments, a single material may function to provide both fluid distribution and fluid storage.

As used herein, the term "front" refers to the portion of an article that is intended to be positioned proximate the front of a wearer. The term "rear" refers to the portion of an article that is intended to be positioned proximate the back of the wearer. As such, use of the relative term "in front of" means a position in the article more toward the front of the article, while the term "behind" means a position in the article more toward the rear of the article.

As used herein, the term "layers" refers to identifiable components of the absorbent structure, and any structure referred to as a "layer" may actually comprise a laminate or combination of several sheets or webs of materials. As used herein, the term "layer" includes the terms "layers" and "layered." The term "upper" refers to a layer nearest to and facing the wearer; conversely, the term "lower" refers to a layer farthest from and facing away from the wearer. The various members, layers, and structures of absorbent articles may or may not be generally planar in nature, and may be shaped or profiled in any desired configuration.

Figure 1A:
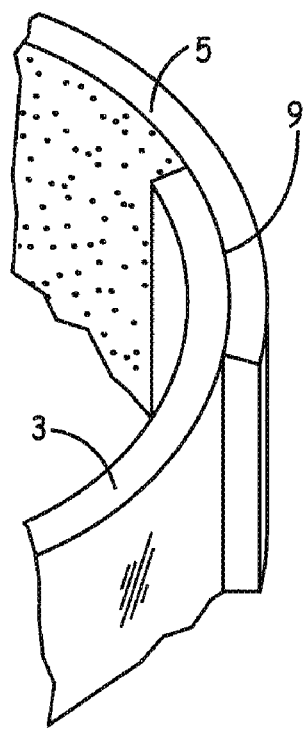
FIG. 1a shows a close up of the seams of FIG. 1.

FIG. 1 shows a finished article 1 produced according to a method such as disclosed herein. Specifically, FIG. 1 shows a disposable absorbent article of the pull-on type having a front panel 3 and a back panel 5. The front panel and the back panel are joined together at the area of overlapping side seams 7, 9 to form a three dimensional disposable garment having leg openings 11, 13 and a waist opening 15. The side seams 7, 9 are formed by overlapping parts of the front panel 3 and the back panel 5. FIG. 1a is a close up of the overlapping seams 7, 9. Overlapping side seams may have favorable characteristics with respect to shear strength (in the plane of the front and back panels) and can, in case the undergarment is a disposable absorbent article, be easily torn apart for removal of a used article from the wearer. The waist opening 15 and the leg openings 11, 13 may be elasticized to contract and snugly fit around the waist and legs of the wearer and to provide gasketing seals that prevent liquids of leaking from the garment 1.

Figure 2:
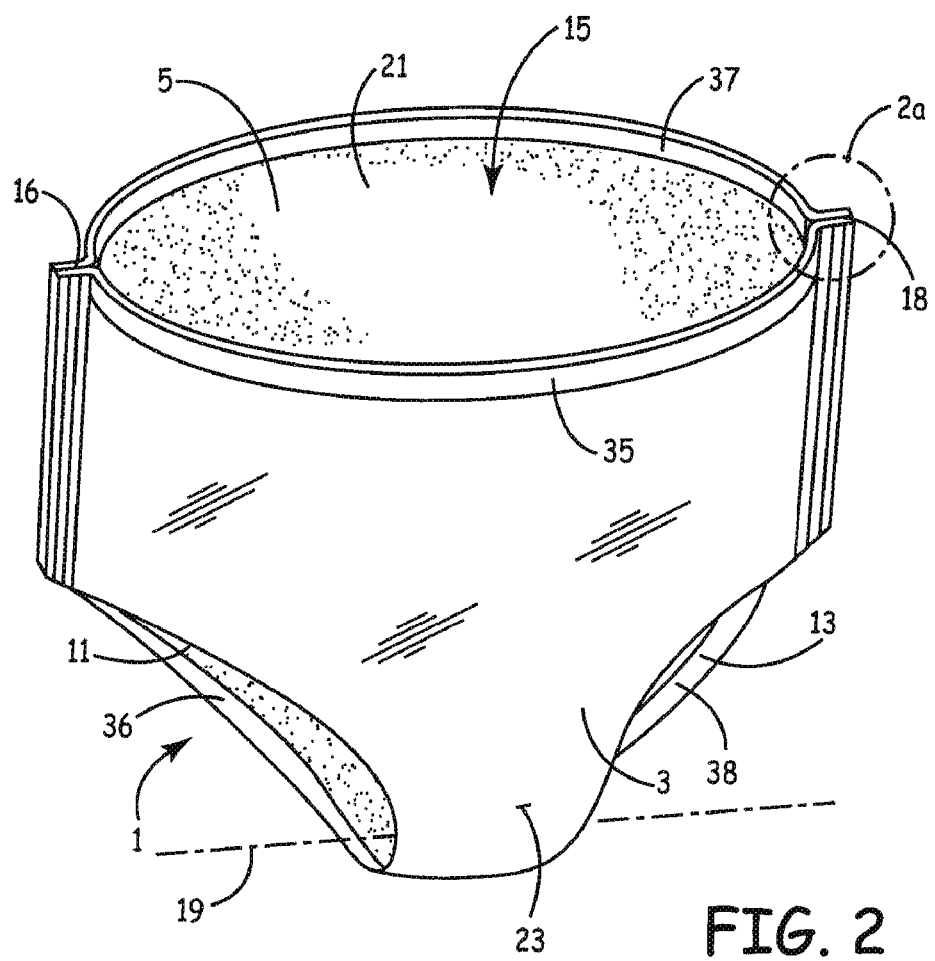
FIG. 2 shows an article having butt-type side seams.
Figure 2A:
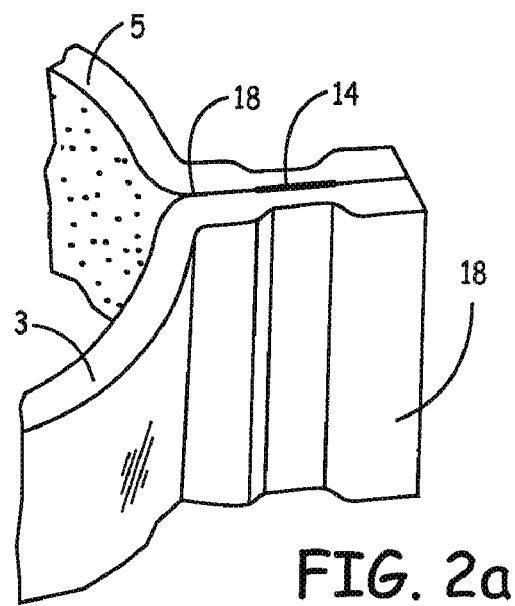
FIG. 2a shows a close up of the seams of FIG. 2.

FIG. 2 shows an article 1 having outwardly located butt-type seams 16, 18. The butt-type seams 16, 18 are made by folding the pre-form, or blank, from which the article 1 is formed along its transverse center line 19 and superimposing the sealing areas that are located on the same surface of the blank in a face-to-face relationship. As shown, the sealing line 14 of the butt-type seam may be located inboard from the outer periphery and leaves the outer edges of the seam unattached in order to maintain a soft edge. FIG. 2a is a close-up of the butt-type seams 16, 18. Alternatively, the butt-type side seams 16, 18 may be located on the inside of the undergarment 1. Inner seams can be obtained when the pre-form, or blank, of the undergarment (described more fully below) is folded along its transverse center line 19 so that its inner surface if facing outwardly upon formation of the seams. Subsequently, by an inverting step, the seams 16 and 18 are turned inwardly.

Overlapping seams or butt-type seams may be formed by any suitable method, including pressure bonding, ultrasonic bonding, heat sealing, adhesive attachment, mechanical attachment, etc. Adhesive or mechanical attachment may comprise, for example, Velcro-type side seams comprising patches of hook-type and loop-type material. These patches may be located parallel to the sides seams or may be located perpendicular to the seams. Alternatively, the side seams may be joined by adhesive tape extending perpendicularly to the seams. The Velcro-type sealing mechanism or adhesive tape may be attached by the manufacturer to form the article. After the article has been attached on a wearer, the seams can be unfastened for inspection of the inside of the article and can after inspection be re-closed by the user for further use.

The article 1 as shown in FIGS. 1 and 2 may comprise a single layer or multiple layers of woven or nonwoven material, and may comprise a thermoplastic film. The article may form a reusable diaper holder that is to be used in combination with a disposable absorbent insert core. Alternatively, the article may form a unitary disposable absorbent article, in which a backsheet, an absorbent core, and a liquid permeable topsheet are combined to form an integral structure.

Figure 3:
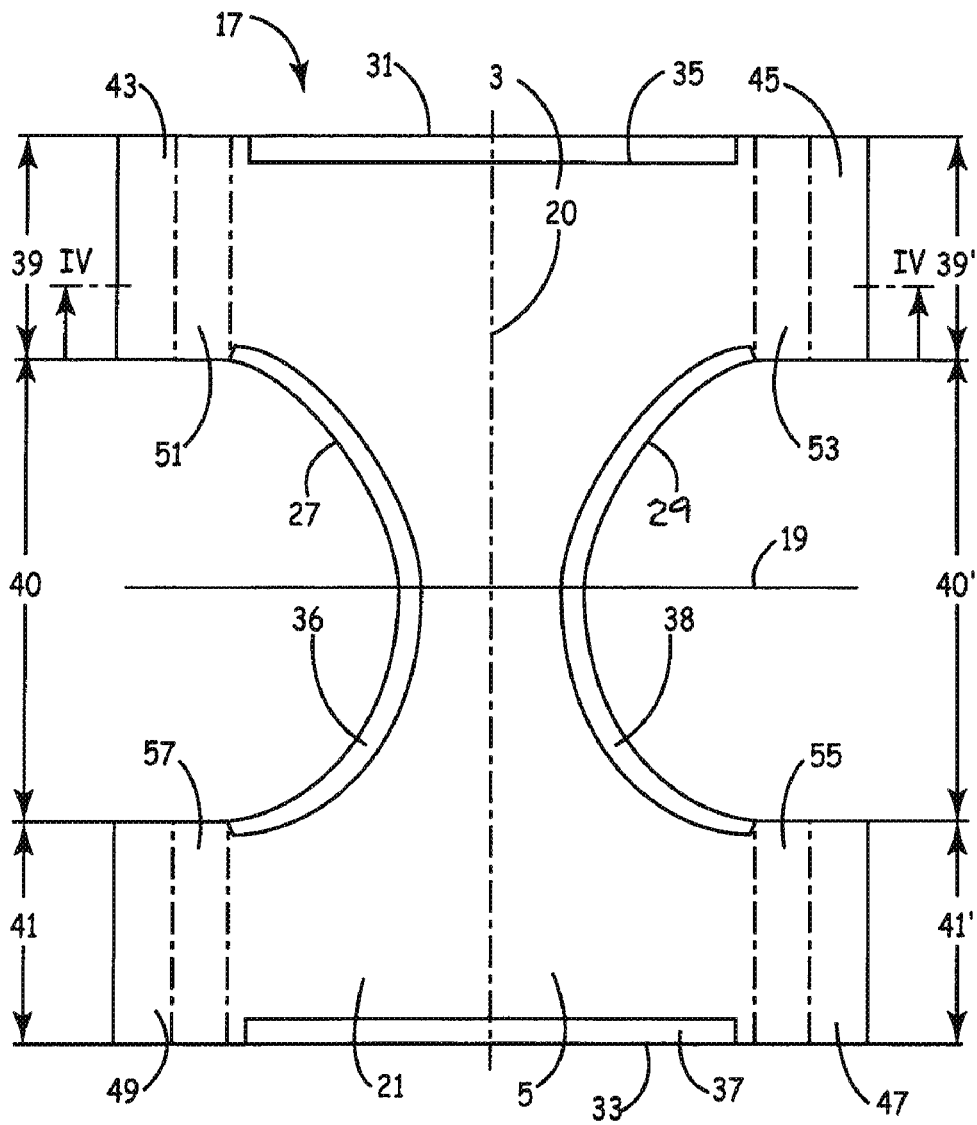
FIG. 3 shows a top plan view of a two-dimensional pre-form for forming an absorbent article having side seams.
Figure 4:
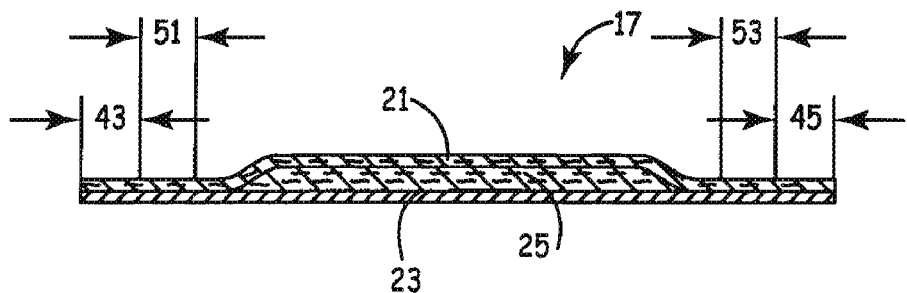
FIG. 4 shows a cross-sectional view of the article of FIG. 3 along line IV-IV.

FIG. 3 shows the pre-form 17 for forming an absorbent article having side seams. FIG. 4 shows a cross-sectional view of the pre-form 17 along the line IV-IV of FIG. 3. The pre-form may alternatively be referred to as the blank. Generally, the blank 17 is processed to form the article. As shown, the blank 17 reflects the article of FIGS. 1 and 2 prior to joining of the front portion of the chassis to the rear portion of the chassis. Generally, the chassis comprises a front portion, a rear portion, and longitudinal side regions. The longitudinal side regions may be seamed via overlapping seams as shown in FIG. 1 or via butt-seams, as shown in FIG. 2. An absorbent assembly such as an absorbent core may be coupled to the chassis.

The pre-form 17 comprises a topsheet 21, a backsheet 23, and an absorbent core 25 interposed between the topsheet and the backsheet. While the topsheet 21, the backsheet 23, and the absorbent core 25 may be assembled in a variety of well known configurations, suitable configurations are described generally in U.S. Pat. Nos. 3,860,003 and 5,151,092, both herein incorporated by reference. As shown, the blank 17 comprises two longitudinal edges 27, 29 and two transverse edges 31, 33. The longitudinal edges 27, 29 and the transverse edges 31, 33 form the periphery of the blank 17. The longitudinal edges 27, 29 extend generally in the direction of the longitudinal center line 20 and comprise cut-out regions that are to form the leg openings 11, 13 of the absorbent article in its assembled state. The blank 17 may further comprise waist elastics 35, 37 and leg elastics 36, 38. Each longitudinal edge 27, 29 comprises a first waist section 39, 39' and a second waist section 41, 41'. The waist sections 39, 39' and 41, 41' of the longitudinal edges 27, 29 are located on both sides of a central crotch section 40, 40' of each edge 27, 29. Each waist section comprises a sealing area 43, 45, 47, 49. The sealing areas 43, 45, 47, 49 may comprise a thermoplastic material. A gripping area 51, 53, 55, 57 may be provided adjacent each sealing area 43, 45, 47, 49.

The absorbent core 25 may comprise any absorbent material capable of absorbing and retaining liquids such as urine and other body exudates. Exemplary but not limiting absorbent structures for use as the absorbent core 25 are described in U.S. Pat. Nos. 4,610,678, 4,673,402, 4,888,231, and 4,834,735, each herein incorporated by reference. The absorbent core 25 may be manufactured in a wide variety of sizes and shapes (e.g., rectangular, hourglass, "T"-shaped, asymmetric, etc.), and from a wide variety of liquid-absorbent materials commonly used in disposable diapers and other absorbent articles. The absorbent core may include multiple layers of absorbent material, each having individual liquid acquisition, acquisition/distribution, or storage/redistribution characteristics, as well as individual shape, width, length, and thickness characteristics. The number and placement of absorbent layers may be varied to achieve desired characteristics such as thinness, softness, flexibility, or beneficial liquid acquisition, distribution, and storage rates, as well as capacity and storage rates, wearer comfort, etc. The components or members of the absorbent core may include laminates or combinations of several sheets or webs of materials. In general, the absorbent core may be made of any suitable absorbent material or combination of materials.

The backsheet 23 is positioned adjacent the garment surface of the absorbent core 25 and may be joined thereto in any suitable manner, including but not limited to adhesive, heat bonds, pressure bonds, ultrasonic bonds, dynamic mechanical bonds, or any other suitable attachment. See, e.g., U.S. Pat. Nos. 4,573,986 and 4,842,666, each herein incorporated by reference. Some portion or all of the backsheet 23 may be generally impervious to liquids (e.g., urine) and may be manufactured from a thin plastic film, although other flexible liquid impervious materials may also be used. The backsheet 23 may thus comprise a woven or nonwoven material, polymeric films such as thermoplastic films of polyethylene or polypropylene, composite materials such as a film-coated nonwoven material, or any other suitable material. The backsheet 23 may be embossed and/or matte finished to provide a more cloth-like appearance. Further, the backsheet 23 may permit vapors to escape from the absorbent core 25 (i.e., breathable) while preventing exudates from passing through the backsheet 23.

The topsheet 21 is positioned adjacent the body facing surface of the absorbent core 25 and may be joined thereto and/or to the backsheet 23. Suitable attachment methods are described with respect to joining the backsheet 23 to the absorbent core 25. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The topsheet 21 may be compliant, soft feeling, and non-irritating to the wearer's skin. Generally, the topsheet 21 may be liquid pervious permitting liquids (e.g., urine) to readily penetrate through its thickness. A suitable topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can include natural fibers, e.g., wood or cotton fibers, synthetic fibers, e.g., polymeric fibers such as polyester, polypropylene, or polyethylene fibers, or a combination of natural and synthetic fibers. In one embodiment, the topsheet is made of a hydrophobic material to isolate the wearer's skin from liquids contained in the absorbent core that is treated on at least one side with a surfactant to allow liquids to readily penetrate therethrough. High loft nonwoven topsheets and apertured formed film topsheets may be used. Apertured formed films are pervious to bodily liquids, non-absorbent, and have a reduced tendency to allow liquids to pass through in a direction away from the absorbent core and thereby rewet the wearer's skin. Thus, the surface of the formed film that is in contact with the body remains dry, thereby reducing bodily soiling and creating a more comfortable feel for the wearer. The body-facing surface of the formed film topsheet can be hydrophilic, thereby helping bodily liquids transfer through the topsheet faster and diminishing the likelihood that liquid will flow off the topsheet rather than flowing into and being absorbed by the absorbent core. There are a number of manufacturing techniques that may be used to manufacture the topsheet 21. For example, the topsheet 21 may be a nonwoven web of fibers spunbonded, carded, wet-laid, meltblown, hydroentangled, thermally bonded, combinations of the above, or the like.

In alternative embodiments, a suitable absorbent core structure 25 without a topsheet may be used to provide desirable results, such as comfort and absorbency, as well as simplicity in manufacturing and material cost savings. For example, the body-side surface of the absorbent core may be made of liquid pervious, soft, compliant, non-irritating materials, thereby making a separate topsheet unnecessary. Such an absorbent core 25 may be used in combination with a backsheet 23 to provide the desired comfort and absorbency in an absorbent article.

In some embodiments, the topsheet 21 and the backsheet 23 are coextensive and have length and width dimensions generally larger than those of the absorbent core 25. Alternatively, the topsheet 21 may be slightly smaller than the backsheet 23. The size of the backsheet and/or topsheet may be guided by the size of the absorbent core and the article design selected.

Elastics, including waist elastics 35, 37 and leg elastics 36, 38, may be provided to exert a contracting force on the article so that it configures more closely and more comfortably to the wearer. Elastic members can be assembled in a variety of well known configurations, such as those described generally in U.S. Pat. No. 3,860,003, herein incorporated by reference.

The disposable absorbent article may comprise elasticized leg cuffs 36, 38 (see FIGS. 1 and 3) for providing improved containment of liquids and other body exudates. Each elasticized leg cuff may comprise several different embodiments for reducing the leakage of body exudates in the leg regions. The leg cuff can be and is sometimes also referred to as leg bands, side flaps, barrier cuffs, or elastic cuffs. Various cuffs, flaps, and openings are described in U.S. Pat. Nos. 3,860,003, 4,909,803, and 4,695,278, each of which is herein incorporated by reference.

The disposable absorbent article may comprise an elastic waist feature 35, 37 that provides improved fit and containment. The elastic waist feature is that portion or zone of the absorbent article which is intended to elastically expand and contract to dynamically fit the wearer's waist. The elastic waist feature at least extends longitudinally outwardly from at least one of the waist edges of the absorbent core 25 and generally forms at least a portion of the end edge of the blank 17. Thus, waist elastics 35, 37 may be disposed adjacent either or both transverse edges 31, 33 to provide a waistband. Disposable absorbent articles are generally constructed so as to have two elastic waist features 35, 37, one positioned in the first waist region and one positioned in the second waist region, although diapers can be constructed with a single elastic waist feature. The waist elastics 35, 37 may be secured to the article in an elastically contractible condition so that, in a normally unrestrained configuration, these elastic members effectively contract or gather the article. The elastics 35, 37 may extend essentially the entire length of the transverse edges 31, 33 or any other length suitable to provide an elastically contractible line. The length of the waist elastics 35, 37 may be guided by the article's design. In one embodiment illustrated in U.S. Pat. No. 4,515,595, elastic waist elements extend across essentially the entire lateral width of a disposable diaper. Similar waistbands may be useful in designs wherein the elastic waist elements extend across only a portion of the lateral width of an article. While the elastic waist feature or any of its constituent elements can comprise a separate element affixed to the absorbent article, the elastic waist feature may be constructed as an extension of other elements of the diaper such as the backsheet 23 or the topsheet 21, or both the backsheet 23 and the topsheet 21. The at least one elastic waistband 35, 37 may be constructed in a number of different configurations including those described in U.S. Pat. Nos. 4,515,595 and 5,151,092, each incorporated herein by reference.

Figure 14:
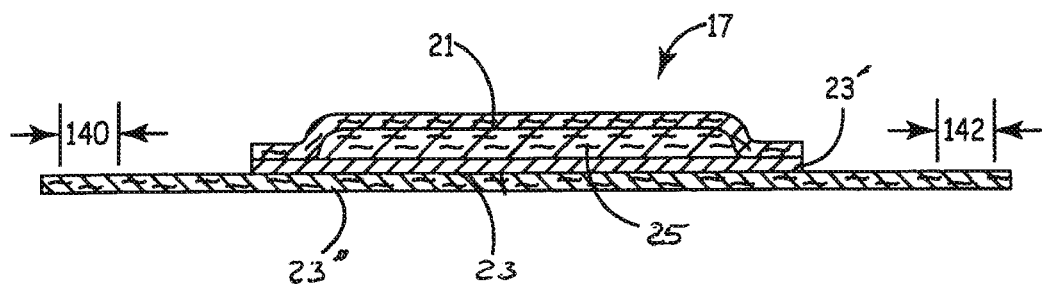
FIGS. 14-18 show cross-sectional views of different embodiments of pre-forms for forming articles having side seams.
Figure 15:
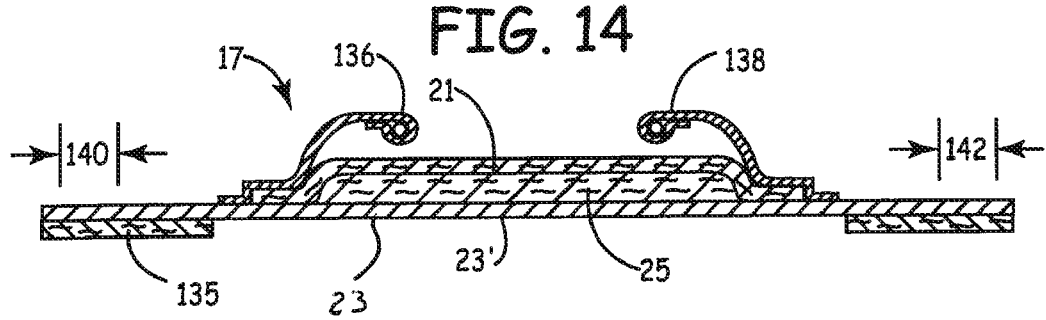
Figure 16:
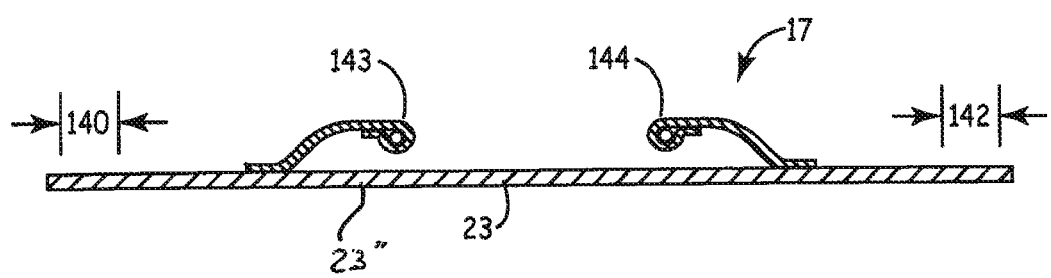
Figure 17:
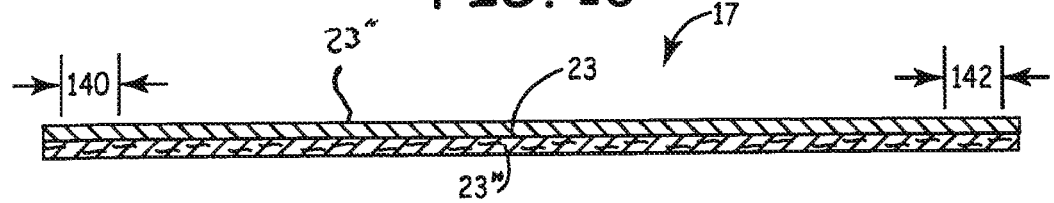
Figure 18:
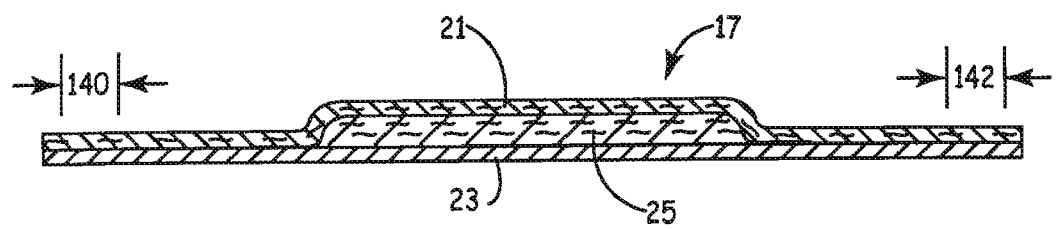

FIGS. 14-18 illustrate different embodiments of blanks 17 suitable for use with the disclosed method and apparatus. FIGS. 14-18 show cross-sectional views along a cross-section that extends parallel to the transverse sides of the blanks 17 and that cuts through two sealing areas 140, 142. The two sealing areas 140, 142 may comprise the waist sealing areas 43, 45 or 47, 49 shown in FIGS. 3 and 4 or may comprise other sealing areas. FIG. 14 shows an embodiment wherein the blank 17 from which the article 1 is formed comprises a topsheet 21, a backsheet 23, and a core 25 interposed between the topsheet and backsheet. The backsheet is formed by a thermoplastic film 23' and a non-woven outer layer 23". The thermoplastic film 23' is not coterminous with the non-woven outer layer 23", such that in each side seam only two layers of the non-woven material 23" are present. The absorbent structure may be made breathable through the use of regions of the non-woven material that are not covered by impermeable film 23'. In the embodiment of FIG. 15, the blank 17 comprises a thermoplastic film backsheet 23, 23' having panels 135, 137 of stretchable material attached thereto. Elasticized stand-up cuffs 136, 138 may be provided on each side of the core 21. In the embodiment of FIG. 16, the blank 17 is intended to form an article in the form of a reusable holder for absorbent insert cores, and comprises a non-woven backsheet 23, 23" and two pocket-forming flaps 143, 144 in which the disposable insert core can be inserted and that serve to hold the insert core in the proper position with respect to the garment. FIG. 17 shows a blank with a backsheet 23, which may comprise a laminate of two non-woven layers 23", 23", both layers extending into the sealing areas 140, 142 for improved strength of the seams. It should be appreciated that the blank in FIG. 17 could also include a backsheet comprising a laminate of a nonwoven layer and a thermoplastic layer, or the backsheet could be any other suitable material or materials. FIG. 18 shows a blank wherein both the topsheet 21 and the backsheet 23 extend into the sealing areas 140, 142 to form reinforced side seams.

Figure 5A:
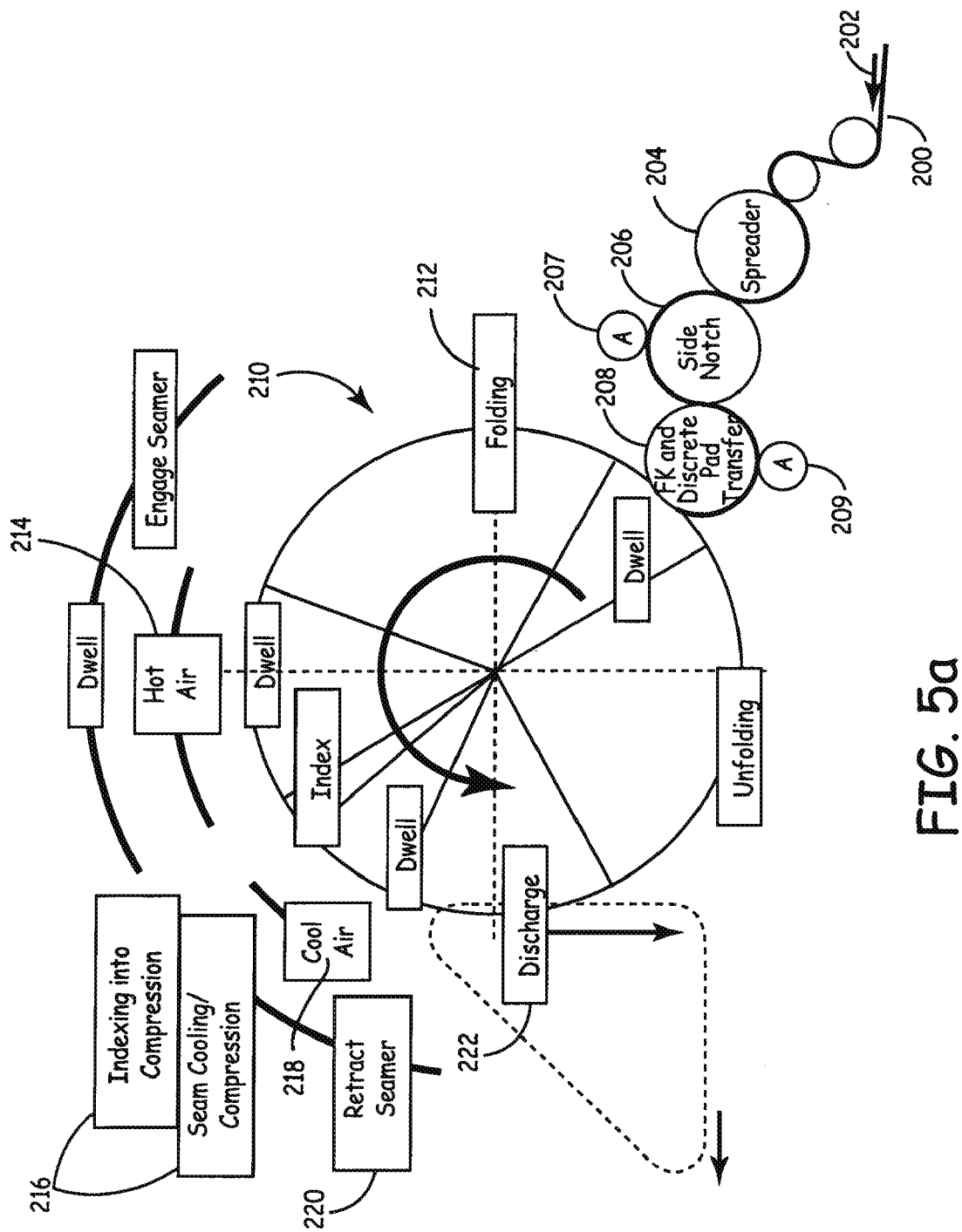
FIG. 5a shows a process diagram of a processing wheel for forming seamed articles in accordance with one embodiment.
Figure 5B:
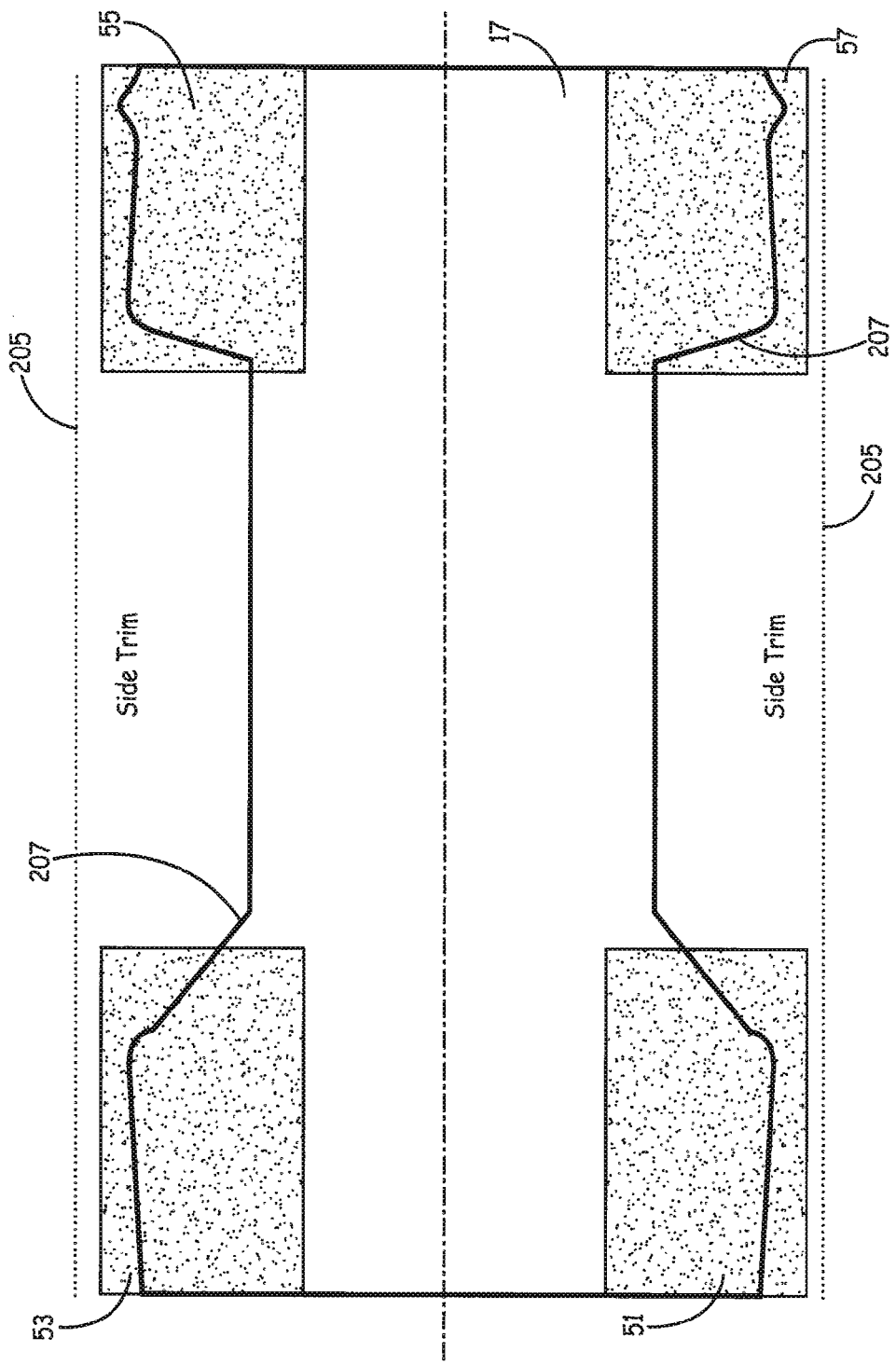
FIG. 5b shows a blank after side notching is performed in accordance with one embodiment.
Figure 5C:
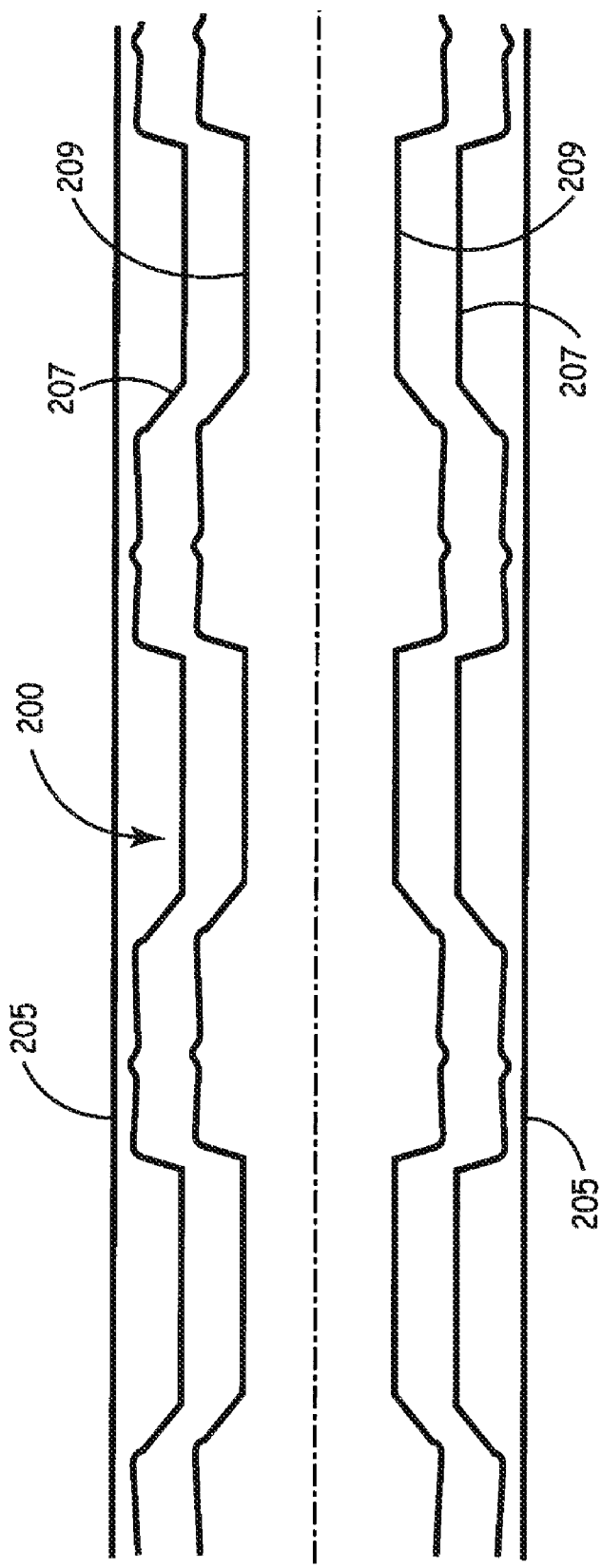
FIG. 5c shows a continuous web after side notching is performed in accordance with one embodiment.

FIG. 5a illustrates a schematic view of a process for forming an absorbent article having side seams. Generally, a continuous web is cut into individual blanks and the individual blanks are loaded onto a processing wheel and processed, including side seaming, to form individual articles. In one embodiment, the continuous web 200 is fed along a conveyor 202 to a spreader 204, where the continuous web 200 is spread for cutting. More precisely, the waist band portions of the continuous web are spread. After spreading, the continuous web undergoes side notching 206. Side notching comprises shaping the continuous web 200 such that individual blanks cut from the continuous web will have contours that ultimately fit the legs of the wearer in the finished article. Generally, side notching comprises removing trim and shaping the side edges of the continuous web into an hourglass form. FIG. 5b illustrates a blank 17 after side notching. The dotted lines 205 illustrate the sides of the blank 17 before side notching and the curved solid lines 207 illustrate the sides of the blank 17 after side notching. FIG. 5c illustrates a continuous web 200 after side notching. Lines 205 represent the sides of the continuous web before side notching. Lines 207 represent the sides of the continuous web after side notching. The space between lines 205 and lines 207 is the trim. An inner notched portion 209 is nested within the side notching of lines 207.

Referring again to FIG. 5a, after side notching 206, the continuous web 200 undergoes a final knife cut 208 to separate the continuous web into individual blanks 17. The final knife cut 208 is done between the trailing edge of one article and the leading edge of another. The final knife cut 208 may be done using a rotating knife. Side notching and final knife cut may be performed separately or may be performed together. As shown, anvils 207, 209 may be provided to perform side notching 206 and final knife cut 208, respectively. Alternatively, a single anvil may be provided to perform both the side notching 206 and the final knife cut 208 or an alternative cutting mechanism may be used for either or both cuts. After the final knife cut 208, whether performed with or separately from side notching, the individual blanks are transferred to a processing wheel 210. As discussed in more detail below, the individual blanks may be transferred to one or more transferring elements on the processing wheel 210. On the processing wheel 210, the individual blanks are folded 212 and seamed. Folding generally occurs in two directions: in the machine direction to cause U-shape of the article and along the side panels to cause the side panels to overlap. Seaming may comprise using a heat exchanger and a compression tool, or any other suitable technique, as described above. The heat exchanger 214 forces hot air against the folded blanks. The compression tool 216 presses the side seams. Cool air 218 may be applied to the folded, seamed blanks to cool the blanks during compression 216. When sealing is done by a heat sealer, such as shown in FIG. 5a, heating up and cooling down time for the side seam material may be allowed. In one embodiment, the heat sealer utilizes about 700 ms sealing time. After cooling, the seamer is removed 220 and the articles are discharged 222.

Figure 5E:
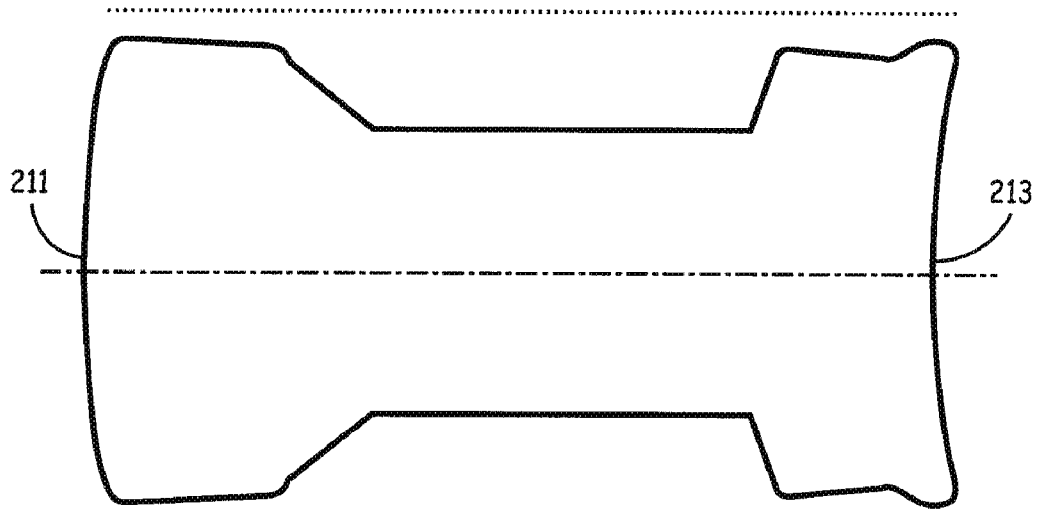
FIG. 5e shows a blank after side notching and a curved final knife cut is performed in accordance with one embodiment.
Figure 5D:
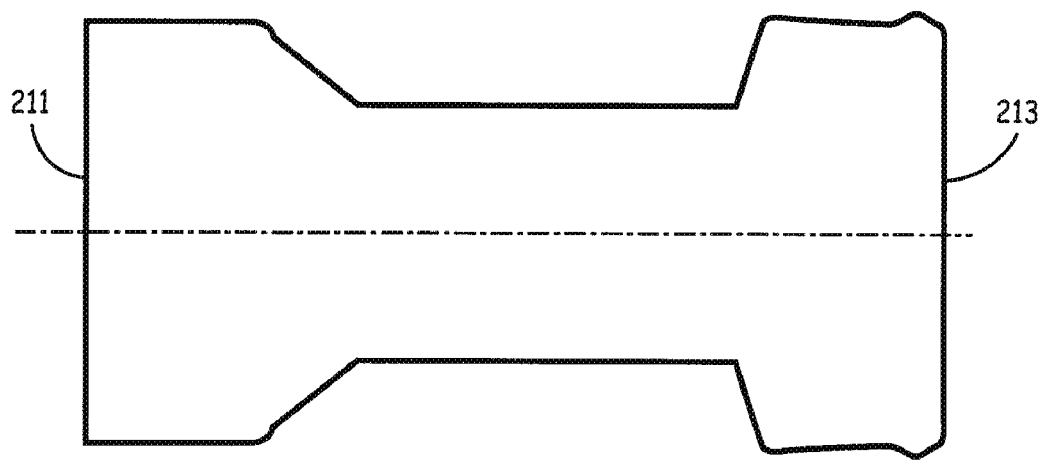
FIG. 5d shows a blank after side notching and a linear final knife cut is performed in accordance with one embodiment.

FIG. 5d illustrates a blank where the final knife cut was done in a straight line. Thus, the leading edge 211 (here the back edge of the article) and the trailing edge 213 (here the front edge of the article) are generally linear. In alternative embodiments, the leading edge may correspond to the front edge of the article and the trailing edge may correspond to the back edge of the article. After performing side notching, there may be cross direction contraction, and after performing the final knife cut, there may be machine directional contraction, both due to elastic elements within the article.

Integrating side notching with the final knife cut imparts a degree of precision to the final knife cut, and thus permits curving of the leading and trailing edges of the article with the final knife cut. This also provides curvature to the waist portions of the article. Performing side notching and final knife cut in one movement reduces variability by preventing movement of the blank between cuts. Further, by integrating side notching with the final knife cut, contraction between cuts is minimized or eliminated. Integration of side notching with the final cut may be done by providing a perimeter die cut. The shape of the front waist edge and the shape of the back waist edge may be the same, may be complementary, or may be unrelated. In one embodiment, shown in FIG. 5e, the front waist edge 213 curves down and the back waist edge curves up 211. Thus, as shown in FIGS. 5f and 5g, a continuous web 200 may be cut into individual blanks 17 using an integrated side notching and final knife cut to result in a curved leading edge 211 and a curved trailing edge 213. In the embodiment of FIG. 5f, no trim is removed between individual blanks 17. In the embodiment of FIG. 5g, trim is removed between individual blanks 17, resulting in spacing of the blanks 17.

Figure 5H:
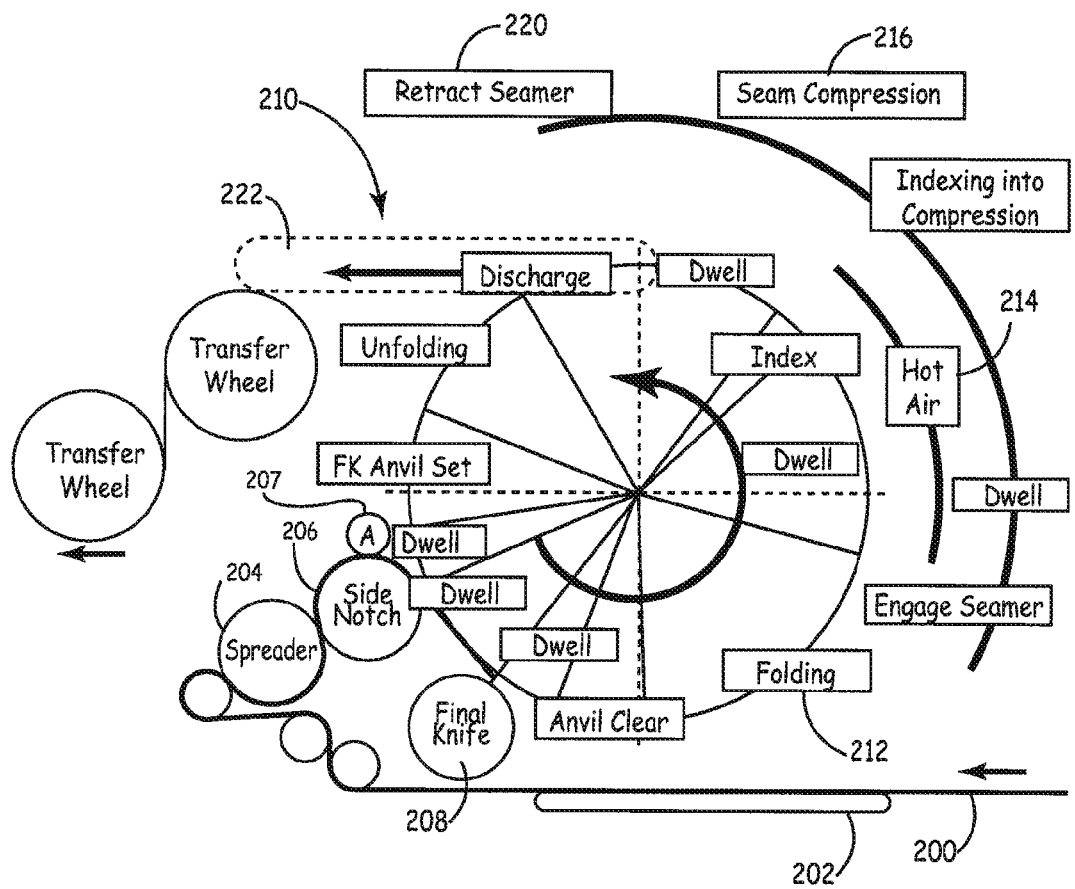
FIG. 5h shows a process diagram of a processing wheel for forming seamed articles as previously done.

It has previously been disclosed to process a continuous web to form side seamed articles. See, for example, U.S. Pat. No. 5,779,831, herein incorporated by reference. As disclosed therein, the continuous web may be cut into individual blanks on the processing wheel 210 and further processed also on the processing wheel 210. Thus, a portion of the process time is devoted to cutting the continuous web into individual blanks FIG. 5h illustrates a processing wheel associated with the processes described in the '831 patent. The continuous web is fed onto the processing wheel and is cut into individual blanks on the processing wheel. As shown, the continuous web 200 is fed along a conveyor 202 to a spreader 204, where the continuous web 200 is spread for cutting. After the spreader, the continuous web undergoes side notching 206, which may be done using an anvil 207, and is transferred to the processing wheel 210. Once loaded on the processing wheel 210, the continuous web 200 undergoes a final knife cut 208 to separate the continuous web into individual blanks 17. The final knife cut 208 is done between the trailing edge of one article and the leading edge of another. After cutting into individual blanks, the individual blanks are folded 212 and seamed. Folding generally occurs in two directions: in the machine direction to cause U-shape of the article and along the side panels to cause the side panels to overlap. Seaming may comprise using a heat exchanger and a compression tool. The heat exchanger 214 forces hot air against the folded blanks. The compression tool 216 presses the side seams. The seamer is removed 220 and the articles are discharged 222.

Thus, in the process of FIG. 5a, the continuous web is cut into individual blanks and the individual blanks are transferred to the processing wheel. In the process of FIG. 5h, the continuous web is transferred to the processing wheel and cut into individual blanks thereon. By cutting the continuous web into individual blanks prior to transfer to the processing wheel, increased processing time is given to folding and seaming by eliminating processing time previously devoted to dwell time pre-final knife cut, time devoted to the final knife cut, and time devoted to final knife anvil clear. This means that the processing wheel can be run faster and throughput can be increased. Further, as discussed above, by cutting the continuous web into individual blanks prior to transfer, it is possible to combine side notching and the final cut to enable shaping of the leading and trailing edges of each blank.

Figure 6A:
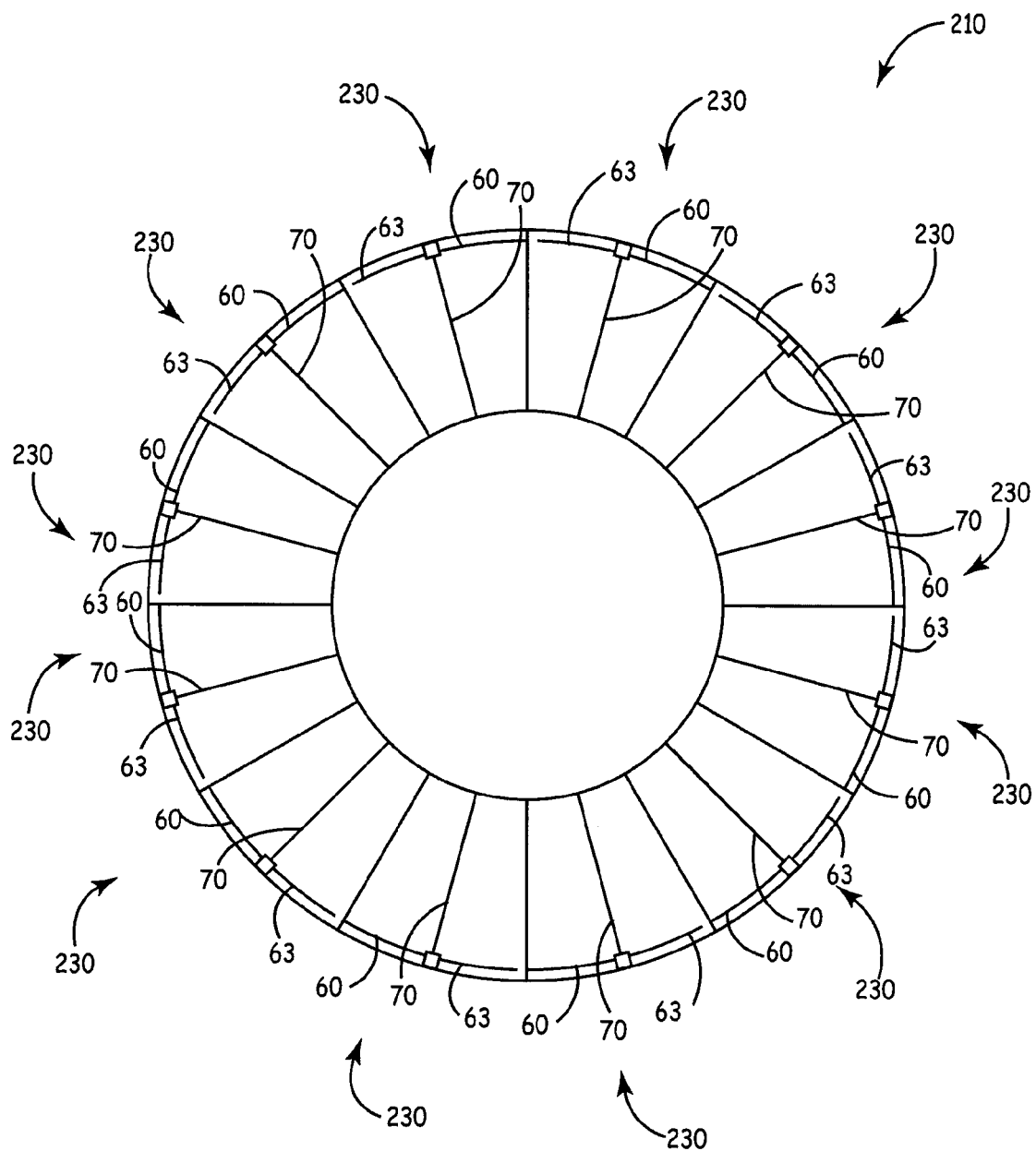
FIG. 6a shows a processing wheel for forming seamed articles in accordance with one embodiment.
Figure 6B:
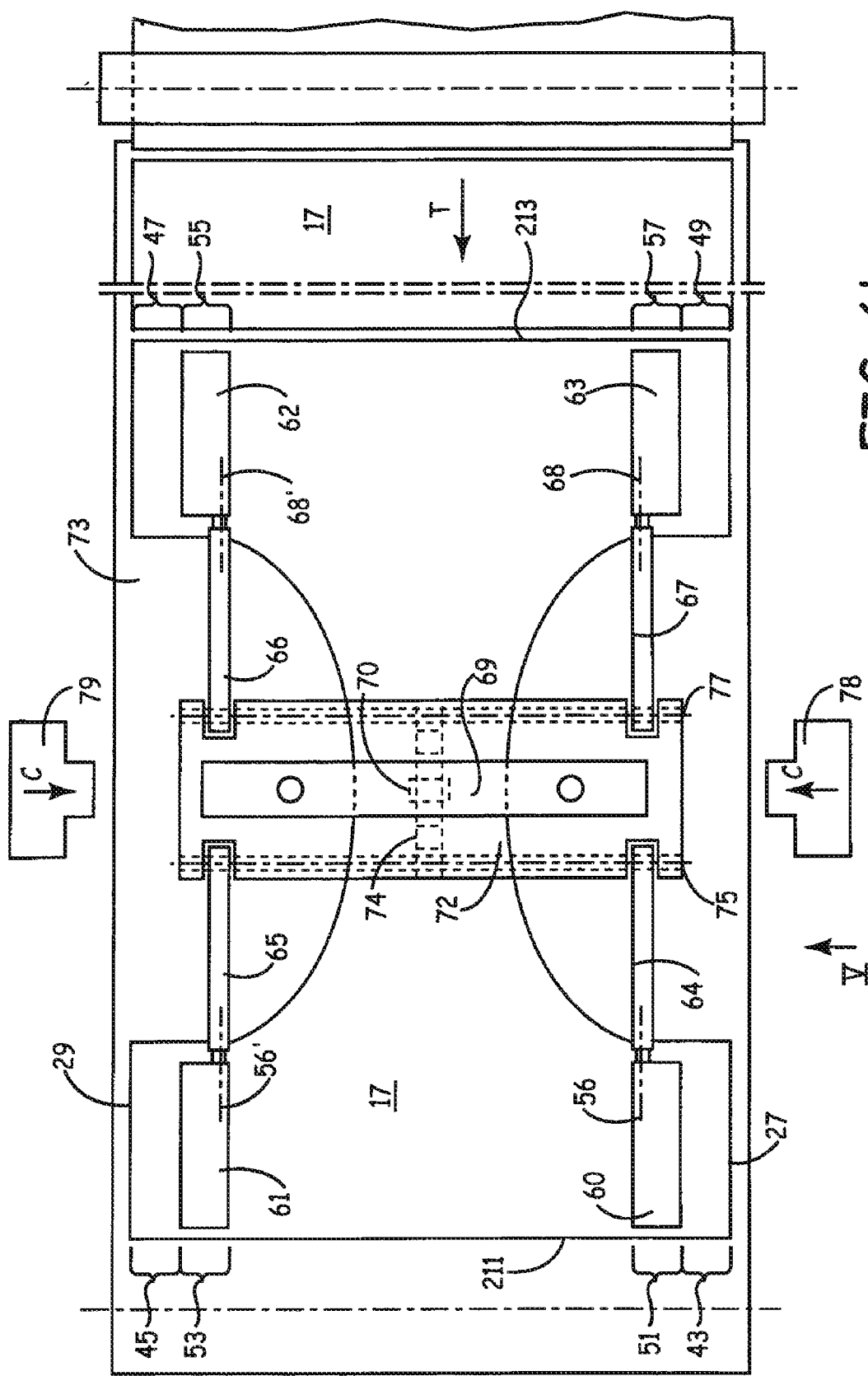
FIG. 6b shows a top elevational view of a processing station as may be provided on a processing wheel of FIG. 6a in accordance with one embodiment.
Figure 6C:
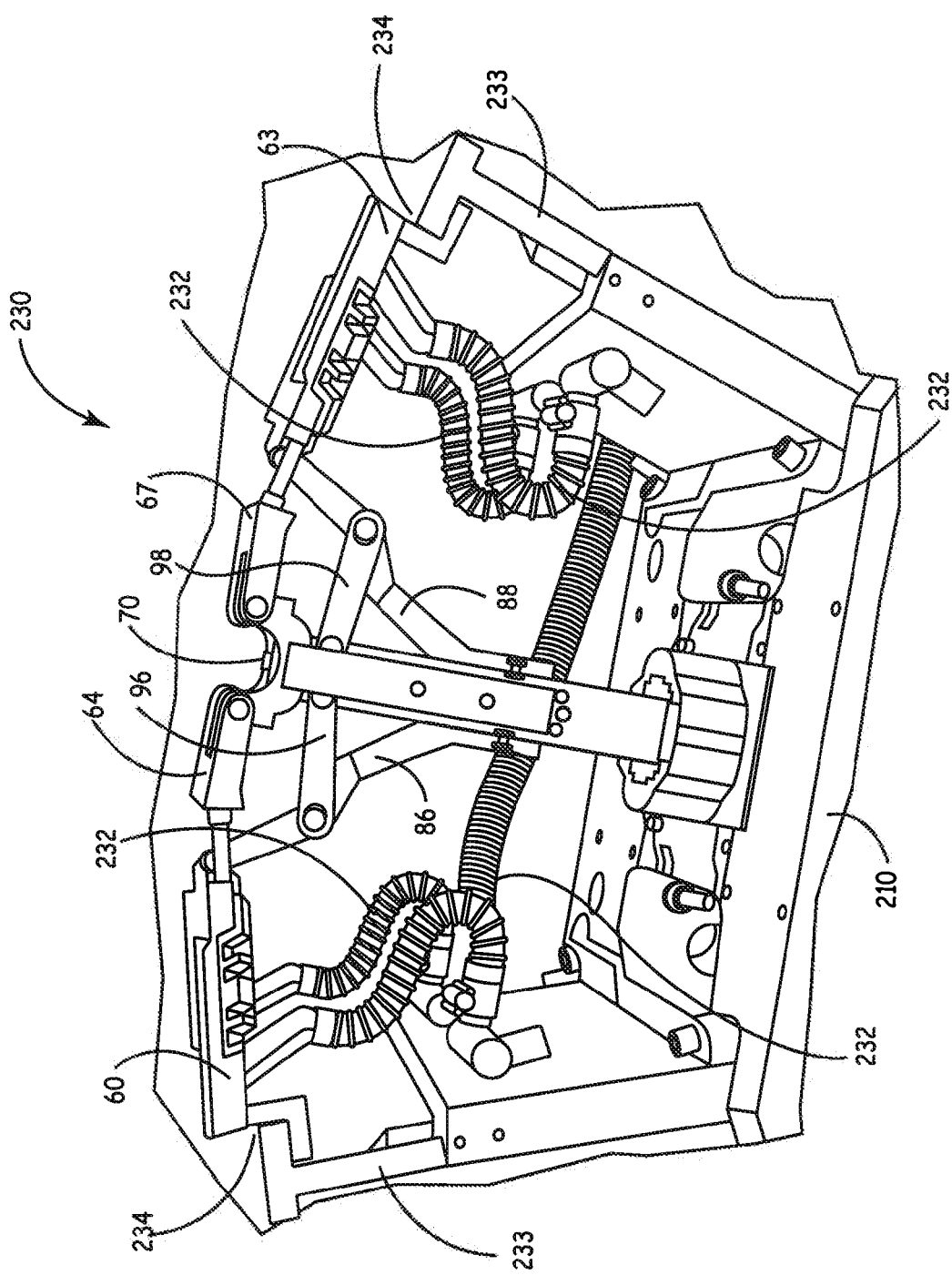
FIG. 6c shows a side perspective view of a processing station as may be provided on a processing wheel of FIG. 6a in accordance with one embodiment.
Figure 6D:
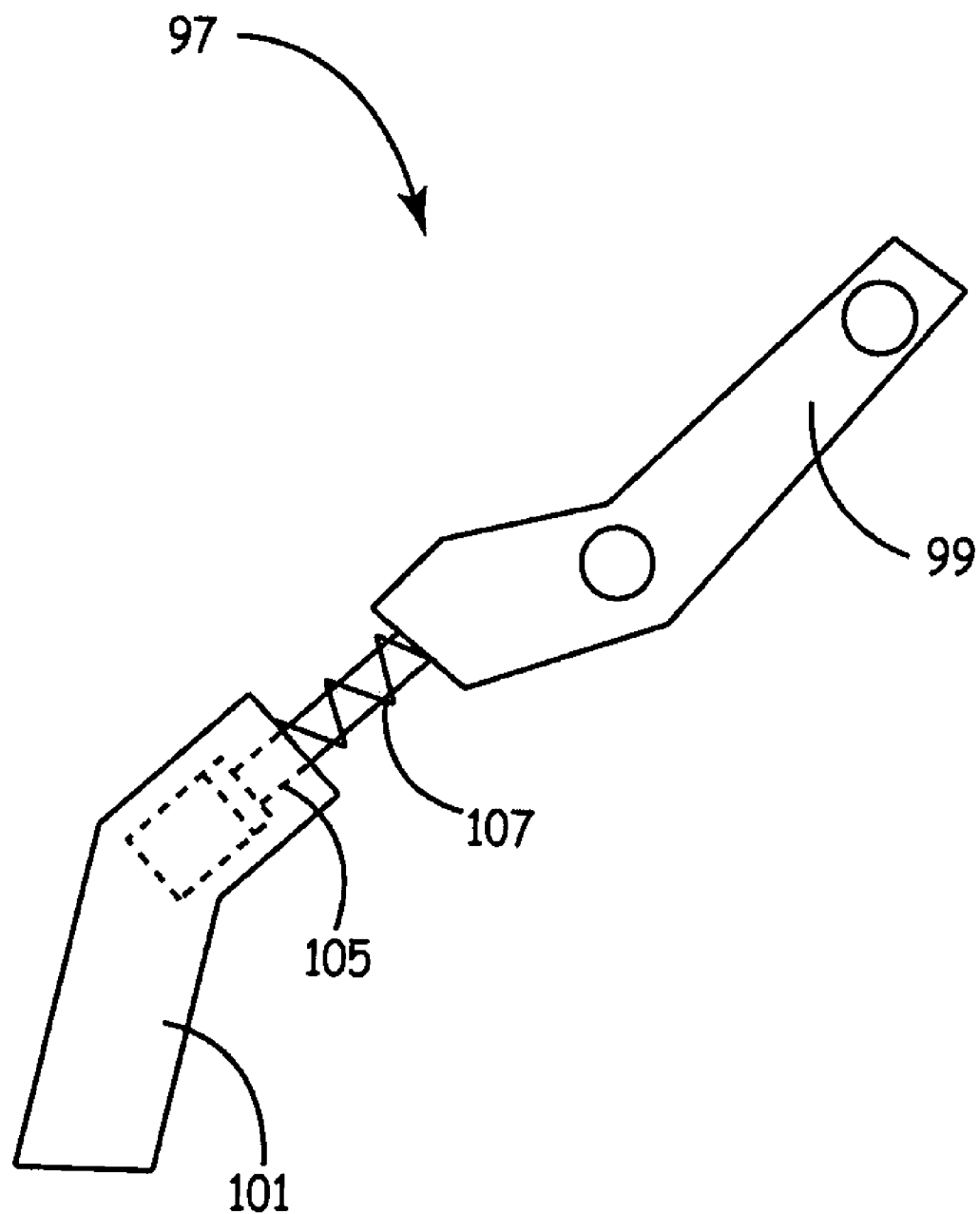
FIG. 6d shows a connecting arm of the processing station of FIG. 6c in accordance with another embodiment.
Figure 6E:
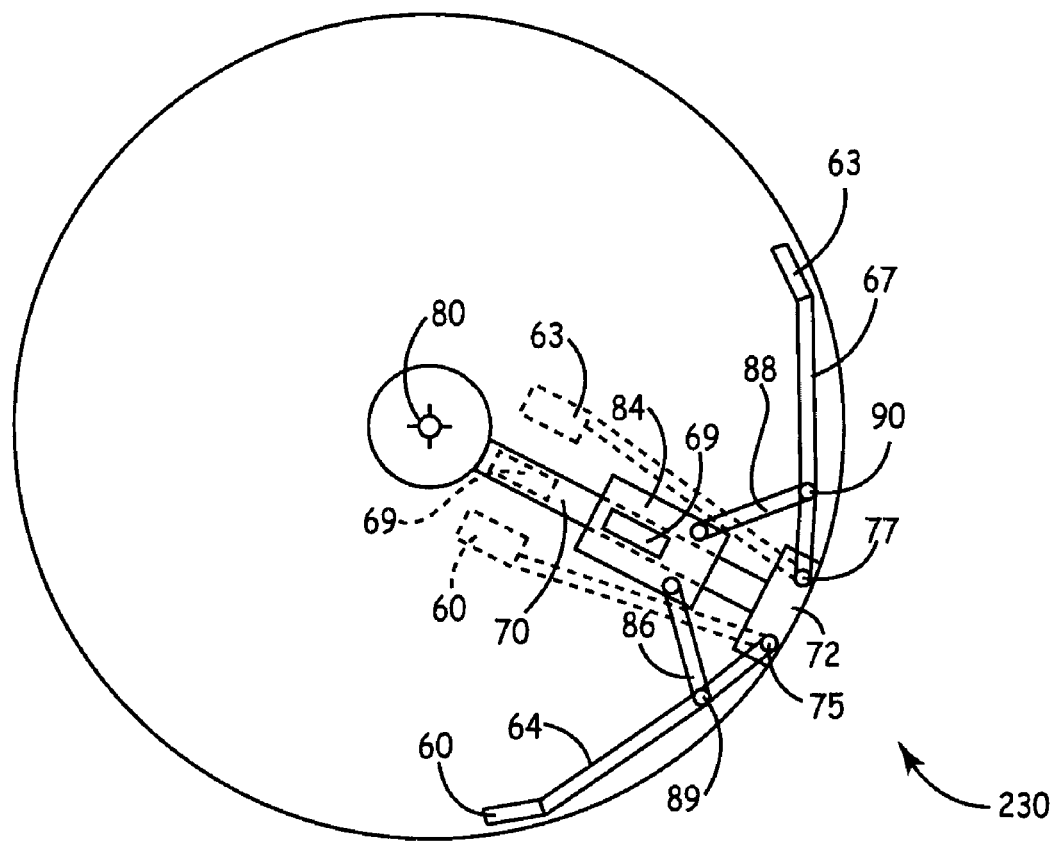
FIG. 6e shows a detailed view of a processing station on a processing wheel in accordance with one embodiment.

FIG. 6a shows a side view of a processing wheel for forming an absorbent article having side seams in accordance with the process of FIG. 5a. FIG. 6b shows a top view of a processing station of the processing wheel of FIG. 5a. FIG. 6c shows a close-up view of a processing station of the processing wheel. FIG. 6d shows a connecting arm of the processing station of FIG. 6c wherein the connecting arm comprises a retractable guide mechanism. FIG. 6e shows a close-up view of a processing station on the processing wheel of FIG. 5a.

The processing wheel 210 comprises at least one processing station 230 for receiving an individual blank 17. The processing wheel 210 may comprise a plurality of processing stations 230. For example, in the embodiment of FIG. 6a, the processing wheel 210 comprises twelve processing stations 230. The individual blank 17 is folded by the processing station 230 and maintained in position while the processing wheel 210 rotates to take the individual blank 17 through processing such as seaming. In alternative embodiments, the apparatus may comprise a conveyor belt or other configuration in lieu of the processing wheel. The individual blanks 17 are transferred in a substantially flattened state from the final knife cut to grippers 60, 61, 62, 63 on a processing station 230 of the processing wheel 210. The continuous web may comprise elastics, such as waist elastics and leg elastics. After cutting into individual blanks, a vacuum force may be exerted on the blank to hold the blank on the cutting unit to prevent the blank from contracting along the elastics, in either or both of the machine direction and the cross direction. Thus, the transfer of the individual blanks onto the processing wheel 210 occurs over a very small gap, sufficiently small to prevent or minimize contraction of the elastics. Generally, a gap of approximately 0 to approximately 9 mm may be used. For the purposes of illustration, a gap of approximately 2 mm is referred to.

In the method and apparatus shown in FIG. 5a, one way to reduce the gap before transfer of the blanks onto the processing wheel is to physically close the gap between the cutting unit or station 208 and the processing wheel 210. Both the cutting unit or station 208 and the processing wheel 210 comprise solid pieces of machinery. The processing wheel 210 includes a plurality of processing stations 230, each being mobile during processing, the vertical positioning of which may vary up to several millimeters. Thus, physically closing the gap between the cutting unit or station 208 and the processing wheel 210 to approximately 2 mm increases a risk of physical contact, which could result in either or both of the cutting unit or station 208 and the processing wheel 210 being damaged. As discussed in more detail below, the processing wheel can be configured in various ways to help reduce the likelihood of such damage.

Returning to the processing wheel 210 and processing stations 230 of FIGS. 6a, 6b, 6c, and 6e, each processing station 230 includes a gripper for gripping the individual blank. As described below, the gripper may comprise a vacuum box, each blank 17 being received by a set of vacuum boxes. The vacuum boxes are air-permeable and runs over a suction box. As used herein, "vacuum" refers to any pressure that is less than ambient, and that is sufficient for the purpose of exerting a holding force on or resistance to the article. As seen most clearly in FIG. 6c, hoses 232 may extend from the suction box 44 to each vacuum box. The blanks 17 are held in a defined position on the vacuum boxes by suction. Suction further prevents the elastic elements 35, 36, 37, 38 in the blanks 17 from contracting during processing of the blanks 17.

Grippers 60, 61, 62, 63 are provided for gripping the individual blanks 17. The grippers 60, 61, 62, 63 are brought in contact with the topsheet 21 of the blanks 17 at four gripping areas 51, 53, 55, 57 (see FIGS. 3 and 5b). As will be described below, the grippers 60, 61, 62, 63 are configured to rotate and move to fold the blanks 17. More particularly, the grippers are rotatably mounted on carrier arms 64, 65, 66, 67 and are adapted to rotate about gripper axes 56, 56', 68, 68'. The carrier arms 64, 65, 66, 67, in turn, are connected to a frame 72 and are adapted to pivot about hinging axes 75, 77. The frame 72 is coupled to a suspension arm 70 within the processing wheel. Generally, the suspension arm 70, for example via association with cam mechanisms, controls the position of the grippers 60, 61, 62, 63. Because the grippers 60, 61, 62, 63 are movable components, a tolerance may be provided with the grippers 60, 61, 62, 63 of about 10 mm, or about 5 mm up and about 5 mm down.

With particular reference to FIG. 6e, the carrier arms 64, 65, 66, 67 are mounted on the frame 72, which forms an upper member. The frame 72 is mounted on the suspension arm 70, which is rotated around a rotation axis 80 generally parallel to hinging axes 75, 77 used for folding the individual blanks. The leading edge 211 of a blank 17 is gripped by the grippers 60, 61 and the trailing edge 213 of the blank 17 may be gripped by the grippers 62, 63. Alternatively, the leading edge 211 of the blank 17 may be gripped by the grippers 62, 63 and the trailing edge 213 of the blank 17 may be gripped by the grippers 60, 61. As such, the geometry of the processing station 230 may be adapted to the length of the blank 17.

A carrier arm actuator is provided for actuating the carrier arms 64, 65, 66, 67 to fold the individual blank 17 in a U-shape. In one embodiment, the carrier arm actuator comprises a lower member 84 and, for each carrier arm, a connecting arm 86, 88. The connecting arms 86, 88 are connected in hinge points 89, 90 to the carrier arms 64, 65, 66, 67 and are hingedly connected to the lower member 84. The lower member 84 is slidably mounted on the suspension arm 70 such that the distance between the frame 72 and the lower member 84 can be varied. An anvil carrier 69 may be provided with the suspension arm 70. The lower member may be moved along the suspension arm 70 to pivot the carrier arms. For example, as shown in FIG. 6e, the carrier arms 64, 65, 66, 67 may be pivoted about the hinging axes 75, 77 toward the anvil carrier 69, as indicated by the dashed lines, by moving the lower member 84 toward the rotation axis 80, while keeping the frame 72 stationary with respect to the suspension arm 70. In an alternative configuration, the carrier arms 64, 65, 66, 67 may be moved to a sealing position by moving the frame 72 along the suspension arm 70 away from a stationary lower member 84. The anvil carrier 69 may be mounted on the suspension arm 70 and rotated together with the carrier arms 64, 65, 66, 67.

Figure 7:
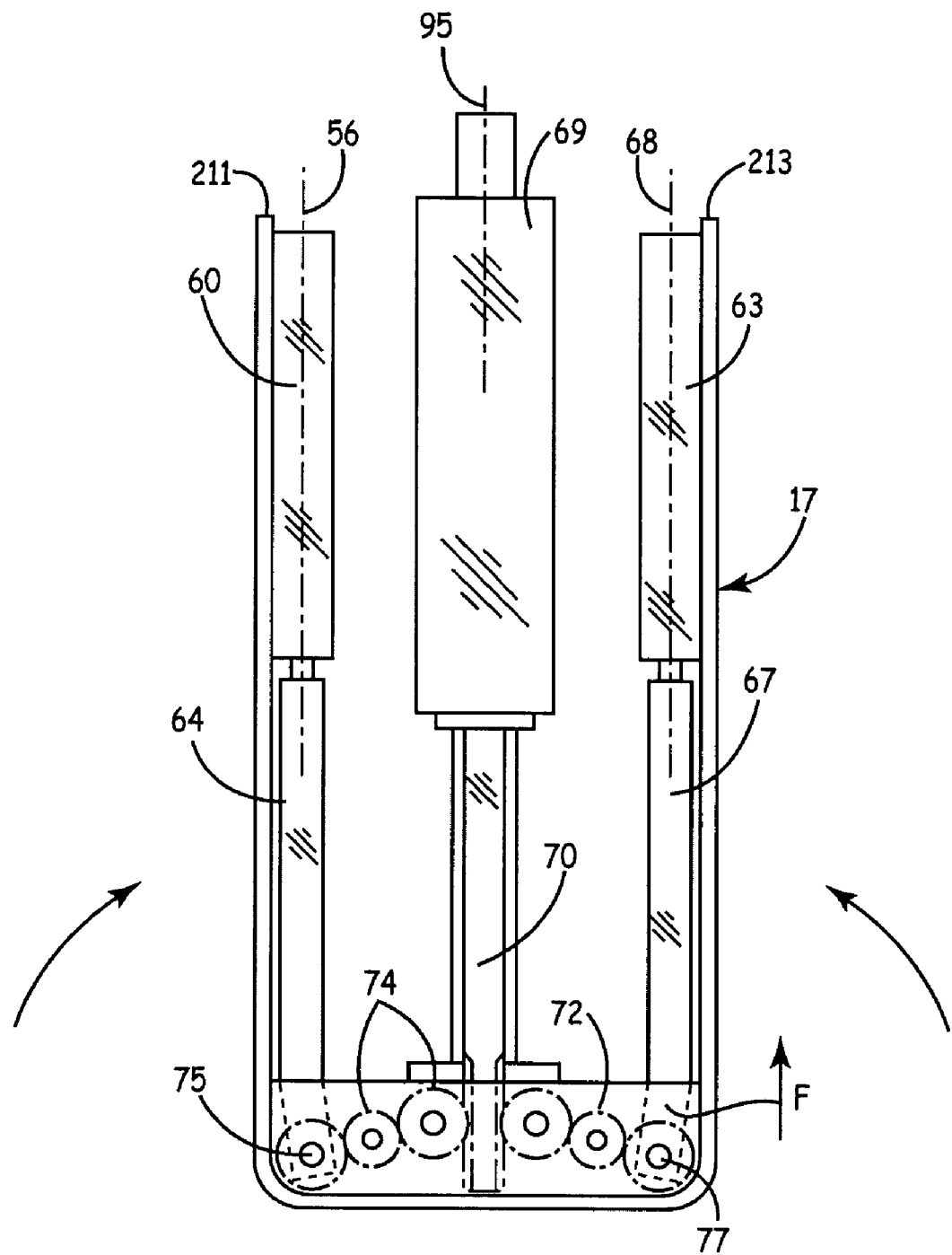
FIGS. 7 and 8 show side elevational views of a processing station in a folded orientation in accordance with one embodiment.
Figure 8:
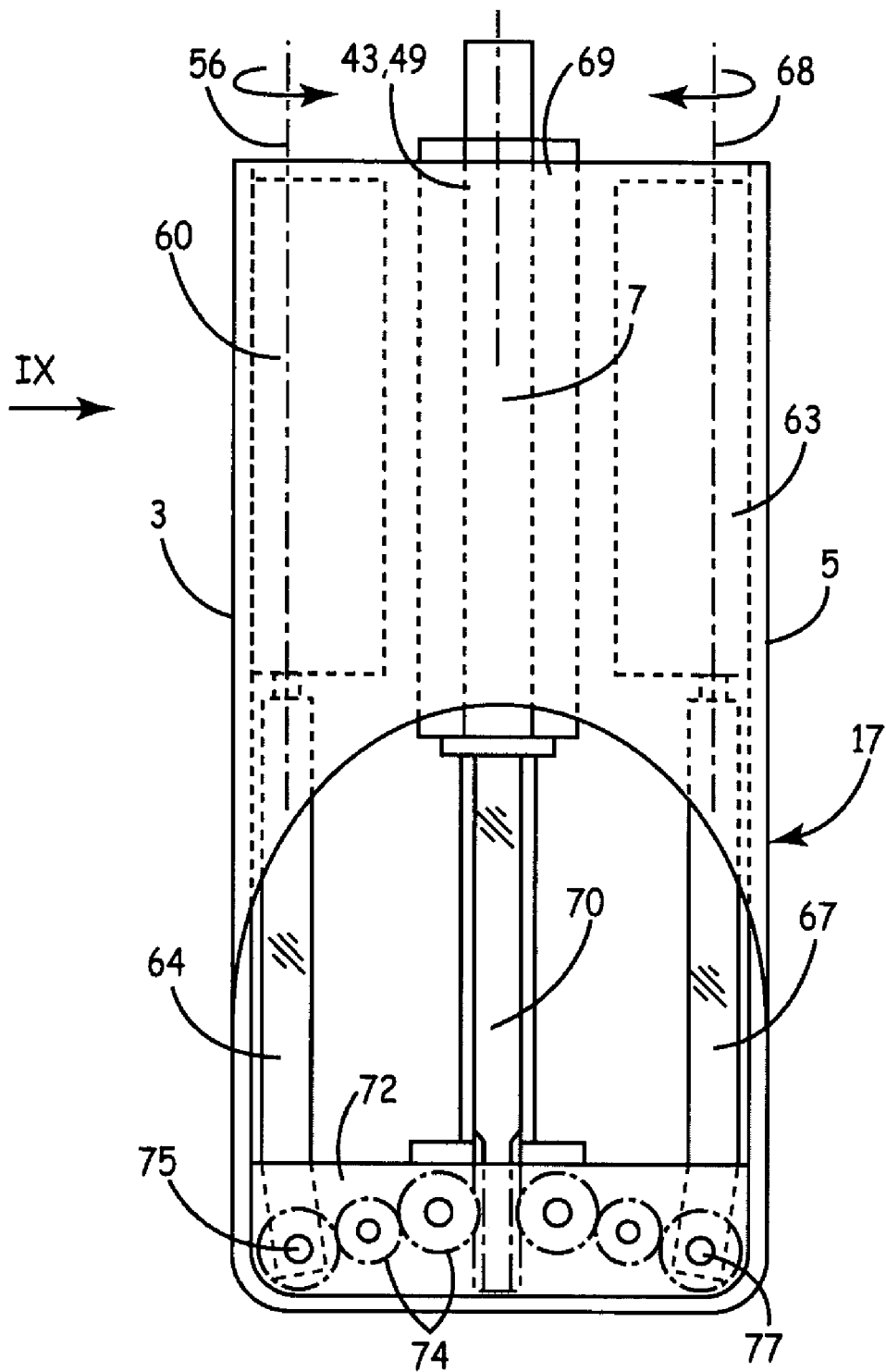

It is to be appreciated that the carrier arm actuator may include other alternative structures, including levers, gears, and/or other suitable structures. For example, FIGS. 7 and 8 show an alternative configuration wherein the carrier arm actuator comprises one or more gears. The carrier arms 64, 65, 66, 67, each connected to grippers 60, 61, 62, 63, can be rotated upwardly around the hinging axes 77, 75 to a position wherein the sealing areas 43, 45, 47, 49 are brought in proximity to the anvil carrier 69, as shown in FIG. 7. In one embodiment, rotation of the carrier arms 64, 65, 66, 67 causes the carrier arms 64, 65, 66, 67 to extend substantially perpendicular to an outer periphery of the processing wheel 210. FIG. 7 illustrates the grippers 60, 63 in the folded configuration. The actuator rotates the carrier arms 64, 65, 66, 67 around the hinging axes 75, 77, and may comprise any suitable actuating structure. In one configuration, the gears 74 may engage a complementary toothed surface on the suspension arm 70. By moving the frame 72 along the arm 70 towards the anvil carrier 69, the carrier arms 64, 65, 66, 67 are rotated upwardly. The direction of rotation of the carrier arms 64, 65, 66, 67 may be varied by selecting an even or uneven number of gears in the actuator. Prior to or during rotation of the carrier arms, the frame 72 and the anvil carrier 69 may in combination be lifted toward a sealing position.

As mentioned above, physically closing the gap between the processing wheel and the final knife station may increase the possibility of physical contact between the processing wheel and the final knife station. To help avoid contact between the processing wheel and the final knife station, the processing wheel may be configured to maintain a predetermined gap or distance between one or more transferring elements thereon and the final knife station.

In some embodiments, the processing wheel includes transferring elements in the form of the grippers 60, 61, 62, 63. Note that in other embodiments including grippers 60, 61, 62, 63, the grippers 60, 61, 62, 63 may not comprise transferring elements. In embodiments wherein the grippers 60, 61, 62, 63 comprise transferring elements, and according to the process shown in FIG. 5a, the individual blanks may be transferred from the final knife station to the grippers 60, 61, 62, 63 on the processing wheel 210. To help maintain the gap between the grippers and the final knife, the processing wheel may include motion stops associated with each of the grippers 60, 61, 62, 63, as shown in FIG. 6c. Thus, while the grippers 60, 61, 62, 63 may have a tolerance exceeding a maximum variance, such that movement of the grippers 60 61, 62, 63 within that tolerance could cause the grippers 60, 61, 62, 63 to contact the final knife station, the motion stop engages the grippers 60, 61, 62, 63 at a point prior to exceeding the maximum variance and thus prior to contact of the grippers 60, 61, 62, 63 with the final knife station. The maximum variance thus may be set at a level wherein, at that variance, the grippers 60, 61, 62, 63 do not contact the final knife station. The location of the motion stop may be precisely controlled to provide a tight tolerance to the grippers 60, 61, 62, 63. Further, the motion stop may be adjustable. In the embodiment shown, the motion stop comprises a wheel portion 233 and a gripper portion 234. The motion stop may be adjustable wherein either the wheel portion 233 or the gripper portion 234 may be adjusted. The wheel portion 233 extends from the processing wheel 210 to a height corresponding with the maximum variance. The gripper portion 234 is associated with a gripper and travels with the gripper. The wheel portion 233 and the gripper portion 234 are configured for engagement. Thus, as the gripper portion 234 reaches the extent of the wheel portion 233, the gripper portion 234 engages the wheel portion 233, stopping the respective gripper 60, 61, 62, 63 from further travel. In the embodiment shown, the wheel portion 233 comprises a T-bar extending upwardly to a height corresponding with a desired tolerance of the grippers 60, 61, 62, 63. The gripper portion 234 comprises a bracket for engaging the T-bar as the grippers 60, 61, 62, 63 reach the desired tolerance. Alternative engaging configurations of motion stops may be used.

In another embodiment, the connecting arms 86, 88 comprise spring-loaded levers such that a force applied to the grippers 60, 61, 62, 63 causes the grippers 60, 61, 62, 63 to deflect via the spring-loaded levers. Allowing the grippers to deflect may help reduce the possibility of damaging various components in some situations. For example, the grippers may deflect to help prevent damage to components on the processing wheel if the carrier arm actuator forces the grippers against the motion stops. In another scenario wherein the grippers contact the final knife station, the grippers may deflect to help prevent damage to components on the processing wheel and/or final knife station. In one embodiment, the spring-loaded levers may be configured as linear guiding mechanisms that control the motion of the grippers 60, 61, 62, 63 and further have the ability to contract in length if contact occurs. Thus, the spring-loaded levers may comprise retractable linear guiding mechanisms. Alternative configurations of retractable linear guiding mechanism may be used in lieu of, or in addition to, spring-loaded levers. FIG. 6d illustrates an alternative embodiment of a retractable linear guiding mechanism wherein the connecting arm 86, 88 of FIG. 6c is formed as a retractable linear guiding mechanism 97. As shown, the retractable linear guiding mechanism 97 comprises first and second bodies 99, 101 coupled by a linear guide 105. A spring 107 is associated with the linear guide 105, for example, provided over the linear guide 105. If contact between the grippers and the final knife station occurs, the retractable linear guiding mechanism 97 may contract along the linear guide 105 via the spring 107.

Figure 6F:
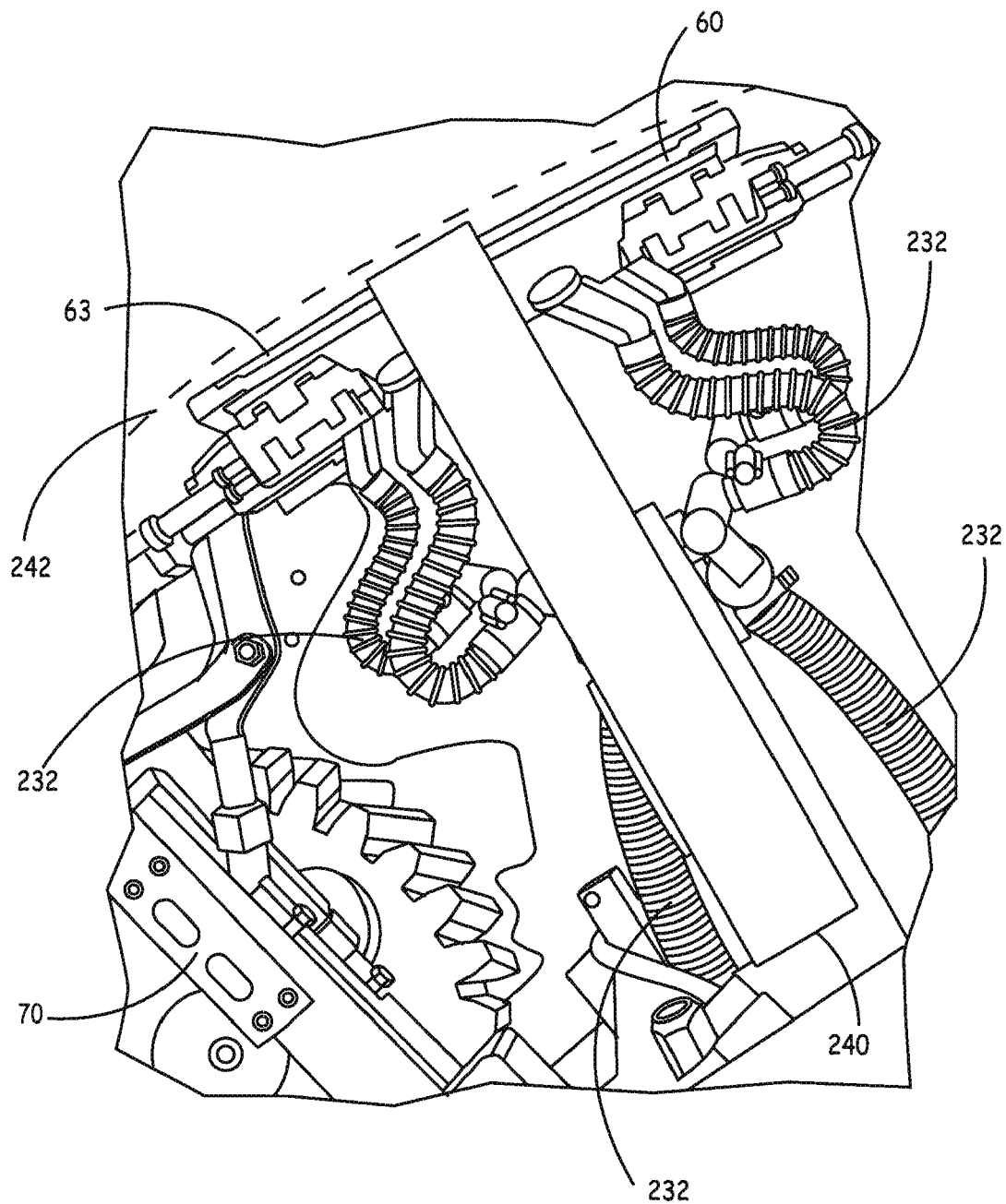
FIG. 6f shows a vacuum transfer bar between processing stations in accordance with one embodiment.

In yet another embodiment, shown in FIG. 6f, the processing wheel includes one or more transfer elements in the form of vacuum transfer bars 240, which may be provided between adjacent processing stations 230 of the processing wheel 210. As such, in the process shown in FIG. 5a, the individual blanks may be transferred from the final knife station to vacuum transfer bars on the processing wheel. As the processing wheel turns, the individual blanks are then transferred to the grippers from the vacuum transfer bars. FIG. 6f illustrates a gripper 63 of a first processing station and a gripper 60 of a second processing station. Thus, in the embodiment shown, each vacuum transfer bar 240 is positioned between adjacent processing stations 230. Two vacuum transfer bars 240 are thus associated with each processing station, one before grippers 60, 61 and one behind grippers 62, 63. A vacuum or negative pressure is drawn through the vacuum transfer bars 240 to receive the individual blanks from the final knife station. As discussed above, the grippers 60, 61, 62, 63 have a tolerance that may result in varying vertical position. The height of the vacuum transfer bars 240 may be precisely controlled to extend past the maximum height of the grippers 60, 61, 62, 63. This height may be set at a height wherein positioning of the grippers below this height will reduce the possibility of the grippers contacting the final knife station. Thus, the individual blanks are transferred from the final knife station to the vacuum transfer bars 240. The dotted line 242 corresponds with the position of the individual blank over the vacuum transfer bars 240, the position of the individual blanks being controlled by the height of the vacuum transfer bars 240. The individual blanks may then be transferred from the vacuum transfer bars 240 to the grippers 60, 61, 62, 63. Any suitable device or method may be used to transfer the individual blanks from the vacuum transfer bars 240 to the grippers 60, 61, 62, 63. Variance of the position of the grippers 60, 61, 62, 63 thus is not relevant in determining the minimum gap between the final knife station and the processing wheel 210. The position of the vacuum transfer bar 240 may be specifically controlled, which in turn controls the gap and tolerances between the final knife station and the processing wheel.

Thus, the distance or gap between the final knife cut and the processing wheel may be controlled or maintained in a variety of ways. As discussed above, retractable linear guiding mechanisms may be provided for controlling the motion of the grippers. The retractable linear guiding mechanisms may comprise spring-loaded levers forming connecting arms such that, if contact occurs between the final knife station and the processing wheel, the grippers retract. In another embodiment, a motion stop may be provided associated with each gripper such that the motion stop engages the gripper at a point prior exceeding a maximum variance. In yet another embodiment, vacuum transfer bars may be provided between adjacent processing stations for receiving the individual blanks. The individual blanks may then be transferred from the vacuum transfer bars to the grippers in any suitable manner. Any other suitable mechanism also may be used to control the distance between the final knife cut and the processing wheel.

As discussed above with reference to FIGS. 6a, 6b, 6c, and 6e, the grippers 60, 61, 62, 63 are adapted to move and to fold the individual blanks 17 as the processing wheel 210 rotates. As previously described, the grippers 60, 61, 62, 63 may be rotatably mounted on carrier arms 64, 65, 66, 67. As such, the grippers are adapted to be rotated about gripper axes 56, 56', 68, 68'. The carrier arms 64, 65, 66, 67, in turn, are connected to a frame 72 and can each be rotated around at least one hinging axis 75, 77. The hinging axes 75, 77 extend generally perpendicular to the rotational travel of the processing wheel 210 generally perpendicular to the carrier arms 64, 65, 66, 67. Thus, the hinging axes 75, 77 extend generally perpendicular to an outer periphery of the processing wheel 210. Folding occurs at the folding portion 212 of the processing wheel 210, as indicated in FIG. 5a. Folding generally occurs in two directions: in the machine direction to cause U-shape of the article and along the side panels to cause the side panels to overlap.

As illustrated in FIG. 8, the sealing areas 45, 47 and 43, 49 of the blank 17 are placed in an overlapping relationship by rotation of each grippers 60, 61, 62, 63 around the gripper axis 56, 56', 68, 68' that extends generally parallel to the carrier arms 64, 65, 66, 67. The overlapped (or superimposed) sealing areas 45, 47 and 43, 49 are contacted with one another between the anvil carrier 69 and the sealer 78, 79. The sealer 78, 79 seals overlapped sealing areas (45, 47 and 43, 49) with one another. In one embodiment, the sealer comprises an ultrasonic conductor. The ultrasonic energy imparted to the sealing areas puts the thermoplastic material of the sealing areas in a heat-softened state, such that upon compression of the sealing areas between the anvil and the conductors an overlapping side seam is formed.

Figure 10A:
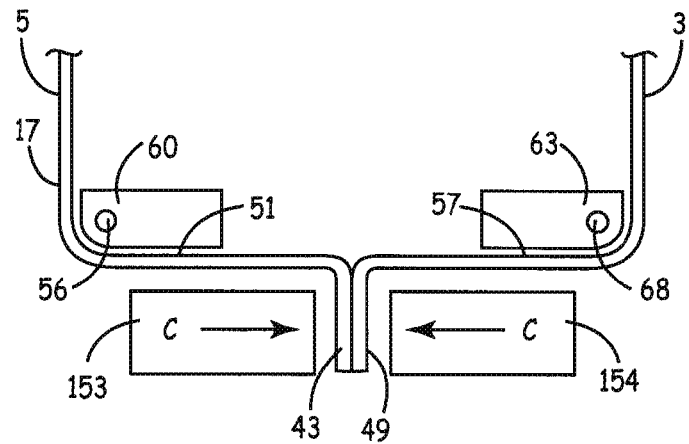
FIG. 10a shows a schematic top view of a gripper and sealer in formation of a butt-type side seam in accordance with one embodiment.
Figure 10B:
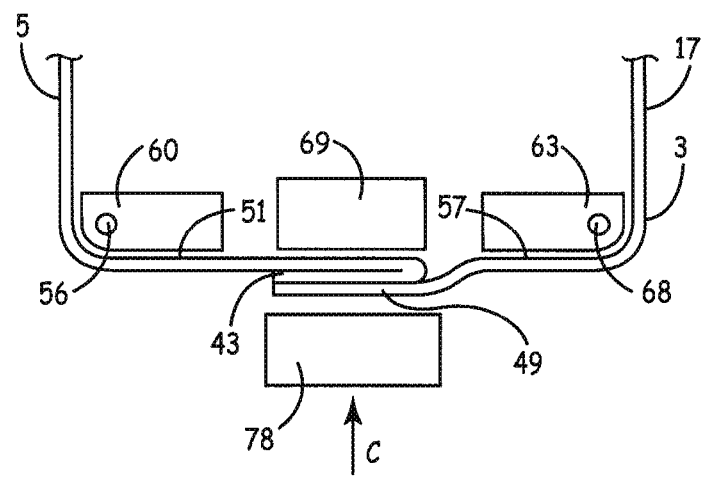
FIG. 10b shows a schematic top view of a gripper and sealer in formation of a combined overlapping and butt-type side seam in accordance with one embodiment.
Figure 10C:
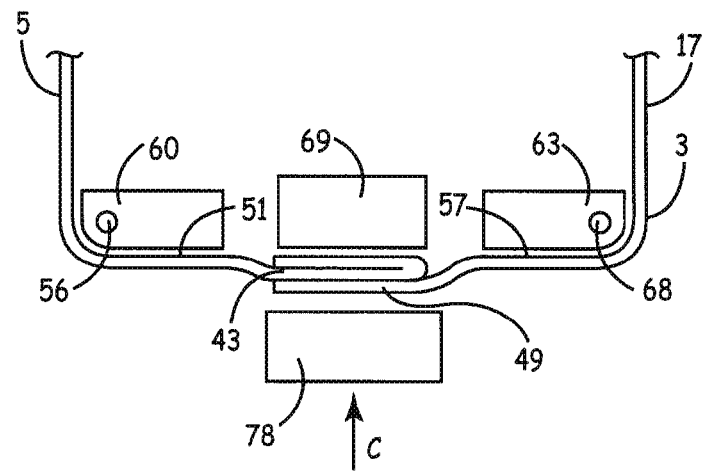
FIG. 10c shows a schematic top view of a gripper and sealer in formation of a three-layer overlapping side seam in accordance with one embodiment.

In alternative embodiments, a butt-type seam may be achieved in lieu of an overlapping seam. Thus, instead of overlapping the sealing areas 43, 49 generally parallel to the plane of the anvil carrier 69, the grippers 61, 62, 63, 64 may be simultaneously rotated around the respective gripper axis 56, 56', 68, 68' in such a way that the sealing areas 43, 49 mutually abut and extend generally perpendicular to the plane of the anvil carrier 69. Sealing may then occur by compressing the abutting sealing areas 43, 49 in a direction generally parallel to the direction of rotation or travel of the processing wheel 210 by a sealer traveling with each processing station 230 at matched speed. Alternative sealing mechanisms may also be used. Different embodiments of overlapping and abutting side seams are shown in FIGS. 10a, 10b, and 10c. The embodiments of FIGS. 10a-10c may be used with any of the embodiments of grippers, motion stops, transfer bars, or other features of processing stations described herein.

In the embodiment of FIG. 6b, sealers 78, 79 are associated with the processing wheel 210, and can be moved in a direction transversely to the direction of travel or rotation to contact the anvil carrier 69. The sealers 78, 79 may comprise heated elements that contact the anvil carrier under any suitable pressure, including but not limited to pressures between 1 and $10^4$ psi. Because the anvil carrier 69 is simultaneously contacted by the sealers 78, 79 from both sides and is squeezed between the sealers, high pressures can be exerted on the side seams without the need for a heavy and rigid suspension of the anvil carrier 69.

In the embodiment of FIG. 6a (corresponding more precisely to the process of FIG. 5a), side seaming is achieved via hot air side seaming. In this embodiment, the sealer comprises a heat exchanger and a seaming tool. The heat exchanger is brought close to overlapping material of the blank, described below, and is used to blow hot air against the blank. After application of heat, a seaming tool, or compression tool, is used to compress the overlapping sides. Thus, the material of the side portions is heated and compressed to form the side seal.

FIG. 10a shows a schematic top view of the position of the sealing areas 43, 49 of the blank 17 upon formation of a butt-type side seam. The sealers 153, 154 compress the sealing areas 43,49 in the direction of the arrows C.

In the embodiment of FIG. 10b, a side seam is formed that is a combination of a butt-type seam as shown in FIG. 2 and an overlapping seam as shown in FIG. 1. The seams of FIG. 10b can be obtained by first placing the sealing areas 43, 49 in an abutting relationship as shown in FIG. 10a, and by subsequently folding over the abutting sealing areas. The folded-over abutting sealing areas 43, 49 are subsequently compressed between the sealer 78 and the anvil carrier 69. The seam formed in this manner is particularly strong, as three layers of material are comprised in the seam.

FIG. 10c shows an overlapping seam comprising three layers of material. In this embodiment, the sealing area 43 is folded over before being placed in a superimposed relationship with the sealing area 49. The folded-over sealing area 43 may be obtained by folding over one of the longitudinal edges 28, 30 of the web 50 before cutting the individual blanks 17 and adhesively, or by heat or ultrasonic sealing, maintaining the longitudinal edge in a doubled-over configuration.

Figure 9:
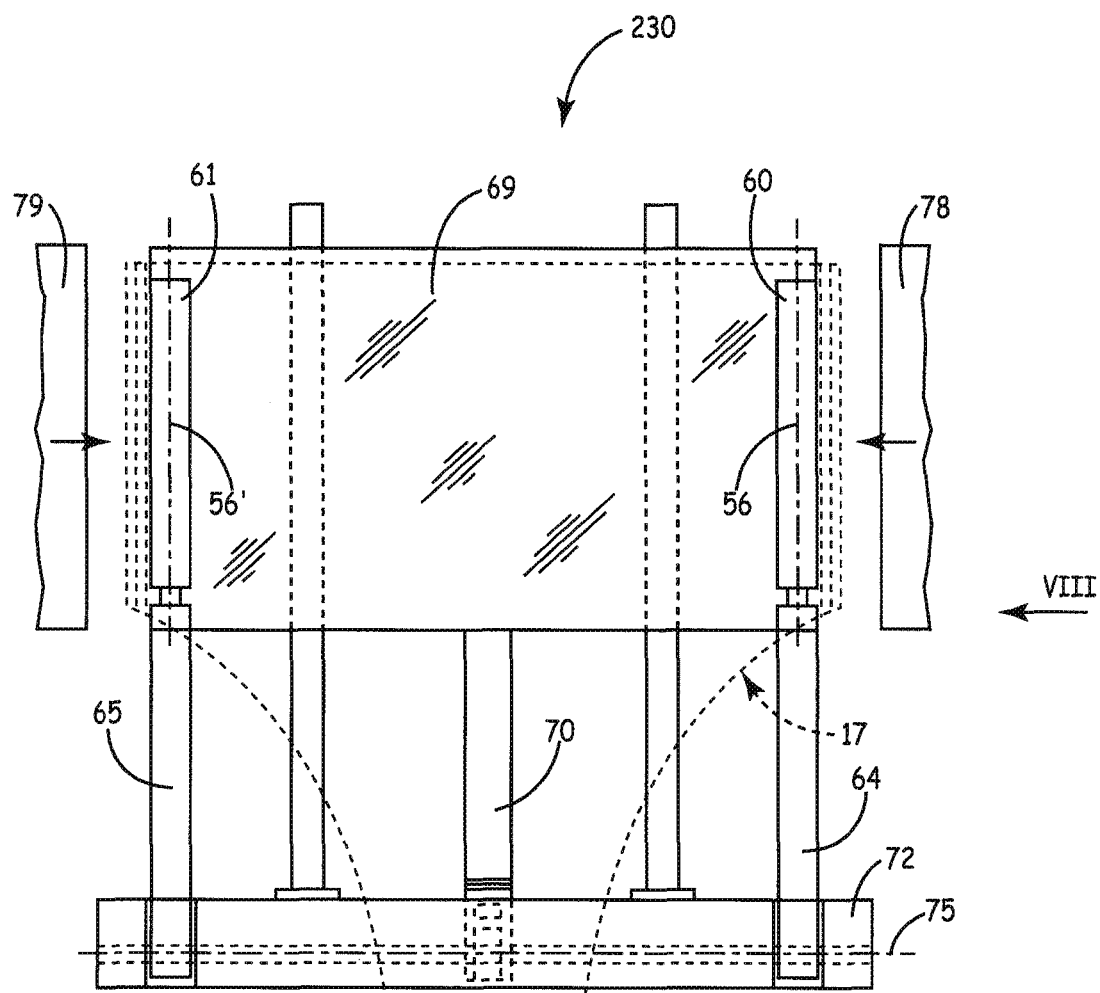
FIG. 9 shows a schematic front elevational view of the processing station as shown in FIG. 8.

FIG. 9 shows a processing station 230 in the sealing position, prior to contacting the ultrasonic conductors 78, 79 with the anvil carrier 69. The blank 17 is indicated by a dashed line. During rotation of the grippers 60, 61 around the gripper axes 56, 56', the blank 17 is stretched and the distance between the grippers 60, 61 may be decreased, for instance by displacing the grippers along the hinging axis 75.

Figure 11:
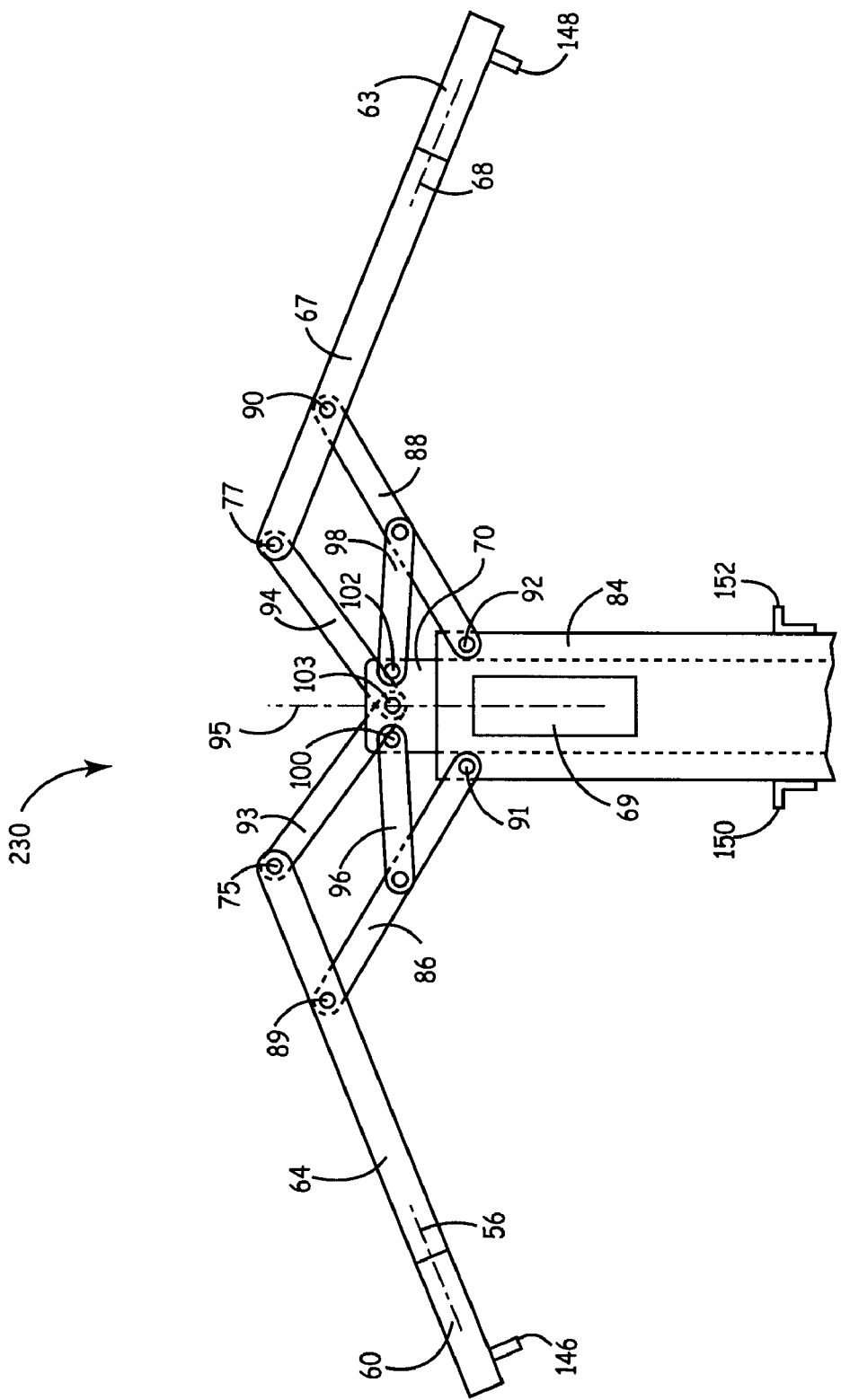
FIG. 11 shows a cross-sectional view of a processing station in a gripping orientation in accordance with one embodiment.
Figure 12:
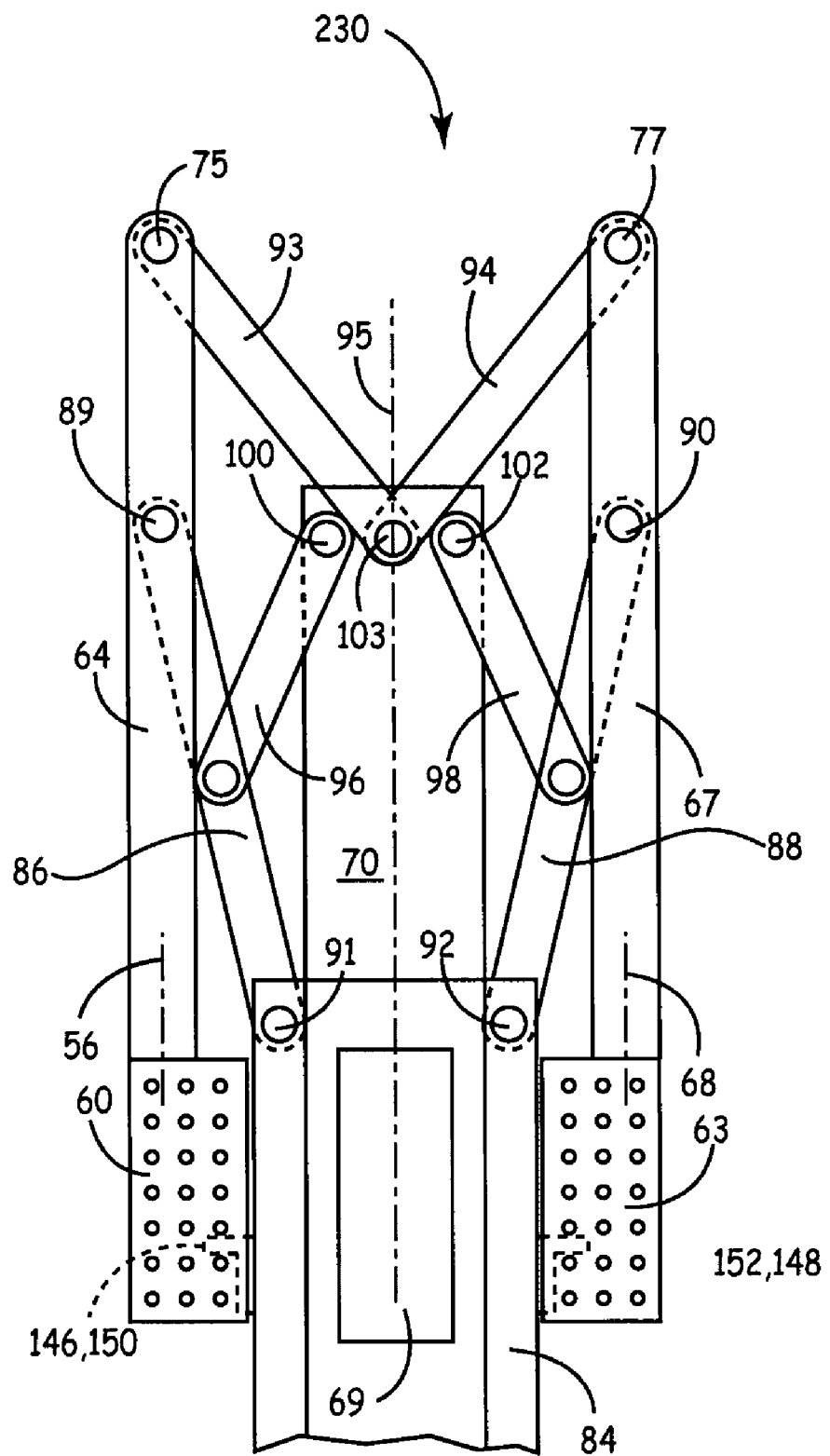
FIG. 12 shows a cross-sectional view of a processing station in a folded orientation in accordance with one embodiment.

In some embodiments, the blank 17 is stretched upon rotation of the carrier arms 64, 65, 66, 67 around the hinging axes 75, 77. Stretching of the blank 17 may be prevented by hinging the carrier arms 64, 65, 66, 67 around hinging axes that lie in the plane of the blank 17. For hinging axes that are not located in the plane of the blank 17 but are above the plane of the blank 17, a length compensator may be provided to prevent or minimize stretching of the blank 17. Thus, to counteract the increase in length of the blank 17 caused by rotating the carrier arms 64-67 upwardly, the processing station 230 may further comprise a length compensator. One example of a length compensator is a telescopic arrangement that varies the length of the carrier arms 64, 65, 66, 67. The length compensator may comprise a suspension of at least one of the hinging axes 75, 77, which causes a varying distance between the hinging axes 75, 77 upon rotation of the carrier arms. This is shown in FIGS. 11 and 12. The embodiments of FIGS. 11 and 12 may be used with any of the embodiments of grippers, motion stops, transfer bars, or other features of processing stations described herein.

FIGS. 11 and 12 show a processing station 230 in the gripping phase and in the sealing phase respectively, including a length compensator. As shown, the length compensator comprises two pivot arms 93, 94 to which the carrier arms 64, 65, 66, 67 are connected. The pivot arms 93, 94 rotate around a central axis 103 connected to the arm 70. The central pivot axis 103 is provided on the center line 95. By rotation of the pivot arms 93, 94 around the central axis 103, the distance between the hinging axes 75, 77, which extend perpendicular to the plane of the drawing of FIGS. 11 and 12, is varied upon rotation of the carrier arms 64-67.

Distance control arms 96, 98 may also be provided. End portions of the distance control arms 96, 98 may be coupled to the arm 70, and opposing end portions of the distance control arms may be coupled to the connecting arms 86, 88. The connecting arms 86, 88 couple to the lower member 84 at pivot points 91, 92, respectively, and to the carrier arms 64, 67 at pivot points 89, 90, respectively. The distance control arms 96, 98 couple the carrier arms 64, 65, 66, 67 with the lower member 84 in such a manner that a single position of the carrier arms 65, 67 corresponds to each position of the lower member 84 along the arm 70.

FIG. 12 shows the lower member 84 in its retracted position wherein the connecting arms 88, 86 have been pulled downwardly generally along the arm 70. The position of the connecting arms 88, 86, the distance control arms 96, 98, and the pivot members 93, 94 is based on the position of the carrier arms 65, 67. When the connecting arms 86, 88 are pulled downward by the lower member 84, the carrier arms 64, 65, 66, 67 are rotated around the hinging axes 75, 77, while the hinging axes are moved along a circle segment that is centered on central axis 103.

As shown in FIGS. 11 and 12, gripper actuators may be provided for rotation of the grippers 60, 61, 62, 63 around the gripper axes 56, 56', 68, 68'. In the embodiment shown, the gripper actuators comprise a protrusion 146, 148 on each gripper 60, 61, 62, 63 and an engaging surface 150, 152 mounted on the arm 70. When the carrier arms 64, 65, 66, 67 are rotated to the sealing position in which they lie adjacent the arm 70, the protrusions 146, 148 are guided along the engaging surfaces 150, 152 such that the grippers 60, 61, 62, 63 are forced to rotate around the gripper axes 56, 56', 68, 68'.

Figure 13:
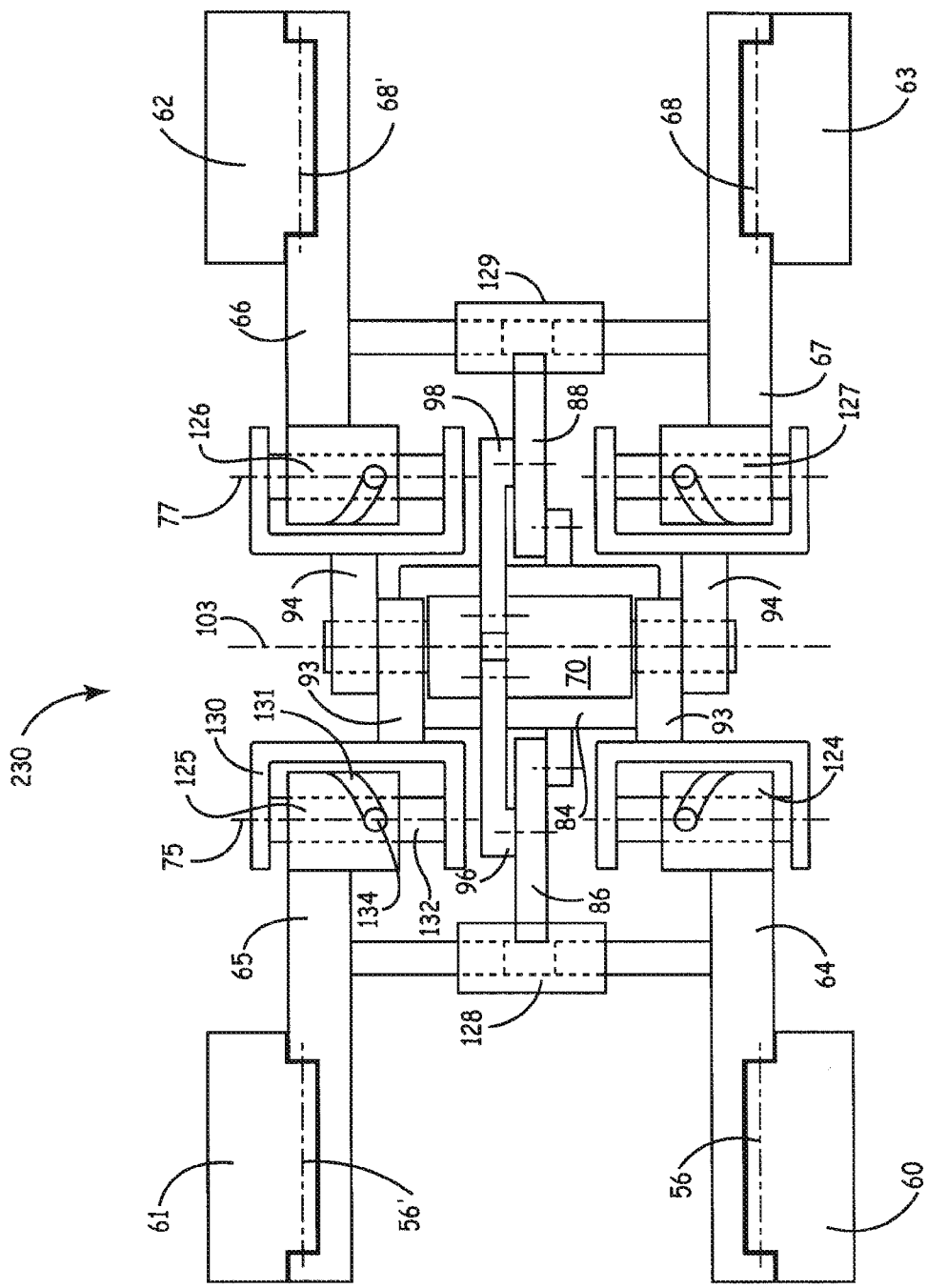
FIG. 13 shows a top cross-sectional view of a processing station in accordance with one embodiment.

FIG. 13 shows a top cross sectional view of a processing station 230, to more clearly depict the width compensator. The embodiment of FIG. 13 may be used with any of the embodiments of grippers, motion stops, transfer bars, or other features of processing stations described herein. Each carrier arm 64, 65, 66, 67 is connected to a grooved member 124, 125, 126, 127. Each carrier arm 64, 65, 66, 67 is mounted in a sleeve 128, 129 that is part of the pivot members 93, 94. The following description is given with respect to gripper 61, but equally applies to the other grippers 60, 62, 63. A grooved member 125 is mounted in a bracket 130, which is connected to the central axis 103 to be jointly rotated with the pivot member 93. The bracket 130 carries an axis 132 generally parallel to the hinging axes (75, 77) on which a pin 134 is located that falls in a groove 131 of the member 125. Upon downward rotation of the carrier arm 65 around the hinging axis 75, the grooved member 125 is axially displaced along the axis 132, such that the distance between the grippers 61 and 62 is decreased.

As discussed previously, the grippers 60, 61, 62, 63 may comprise vacuum grippers such as vacuum boxes. Each vacuum gripper may comprise a generally hollow body or a cavity that has one or more outlets on a gripping surface to contact the gripping areas of the blank. Each hollow body or cavity of the gripper may be connected via a flexible vacuum lead or hose, such as hose 232 shown in FIG. 6c, to a switched vacuum supply.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making an undergarment having side seams from a web, the method comprising:
    providing a cutting unit;
    cutting the web to form a pre-form, the pre-form comprising first and the second transverse edges and two longitudinal edges, each longitudinal edge having two waist sections and a crotch section located intermediate the waist sections, a sealing area located adjacent each waist section;
    transferring the pre-form to at least one transferring element on a processing wheel, the processing wheel comprising T-bars, and the at least one transferring element comprising a plurality of grippers;
    generally maintaining a predetermined distance between the cutting unit and the transferring element by engaging the plurality of grippers with the T-bars to limit movement of the plurality of grippers;
    gripping the pre-form adjacent each waist section in a plurality of gripping areas with the plurality of grippers, each gripping area being located near a respective sealing area,
    jointly rotating the gripping areas to place the transverse edge generally parallel and opposite to the second transverse edge;
    superimposing the sealing areas in a contacting relationship;
    joining the superimposed sealing areas, thus forming the undergarment; and
    releasing the undergarment.

2. The method of claim 1, wherein the at least one transferring element comprises at least one vacuum bar.

3. The method of claim 1, wherein gripping the pre-form adjacent each waist section in a plurality of gripping areas comprises gripping the pre-form adjacent each waist section with the at least one gripper.

4. The method of claim 3, wherein gripping the pre-form adjacent each waist section in a plurality of gripping areas comprises gripping the pre-form adjacent each waist section with the at least one gripper using a vacuum.

5. The method of claim 3, wherein superimposing the sealing areas comprises rotating the at least one gripper around a respective axis of rotation extending generally parallel to the longitudinal sides of the pre-form to place the sealing areas in an overlapping relationship to form overlapping side seams, or in an abutting relationship to form abutting side seams.

6. The method of claim 3, wherein jointly rotating the gripping areas to place the transverse edge generally parallel and opposite to the second transverse edge comprises jointly rotating at least the grippers holding the gripping areas in the region of one of the transverse edges around at least one hinging axis extending substantially parallel to the transverse edges of the pre-form.

7. The method of claim 6, wherein after gripping the pre-form in the gripping areas, at least one of the hinging axes is displaced to prevent stretching the pre-form in the direction of the longitudinal edges.

8. The method of claim 1, wherein cutting the web to form the pre-form comprises performing side notching and a final knife cut, wherein the side notching and final knife cut are done as a single step.

9. The method of claim 1, further comprising forming the web by combining a backsheet, an absorbent core, and a topsheet, such that the undergarment is an absorbent article.

10. The method of claim 1, wherein after gripping the pre-form in the gripping areas, the distance between the gripping areas located along the same transverse edge is decreased to prevent stretching of the pre-form in the direction of the transverse edges.

11. The method of claim 1, wherein joining the superimposed sealing areas comprises heat-sealing.

12. The method of claim 1, wherein the pre-form comprises elastic elements in the transverse direction and the longitudinal direction, and the method comprises maintaining the elastic elements in an extended state at least during the transfer of the pre-form to the processing wheel.

\* \* \* \* \*